United States Patent
Isaacson

(10) Patent No.: US 11,779,734 B2
(45) Date of Patent: Oct. 10, 2023

(54) CATHETER ASSEMBLY

(71) Applicant: Becton, Dickinson and Company, Franklin Lakes, NJ (US)

(72) Inventor: S. Ray Isaacson, Layton, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 375 days.

(21) Appl. No.: 17/039,183

(22) Filed: Sep. 30, 2020

(65) Prior Publication Data

US 2021/0008348 A1    Jan. 14, 2021

Related U.S. Application Data

(63) Continuation of application No. 15/827,967, filed on Nov. 30, 2017, now Pat. No. 10,828,467.

(51) Int. Cl.
*A61M 25/06* (2006.01)
*A61M 5/32* (2006.01)
*A61M 25/00* (2006.01)
*A61M 39/02* (2006.01)

(52) U.S. Cl.
CPC ........ *A61M 25/0618* (2013.01); *A61M 5/321* (2013.01); *A61M 5/3232* (2013.01); *A61M 5/3243* (2013.01); *A61M 5/3273* (2013.01); *A61M 25/0097* (2013.01); *A61M 25/0625* (2013.01); *A61M 25/0631* (2013.01); *A61M 39/02* (2013.01); *A61M 2005/3212* (2013.01); *A61M 2005/3247* (2013.01)

(58) Field of Classification Search
None
See application file for complete search history.

(56) References Cited

U.S. PATENT DOCUMENTS

| 1,470,724 | A | * | 10/1923 | Ginsberg | ............... B43K 23/10 |
| | | | | | 401/91 |
| 4,952,207 | A | | 8/1990 | Lemieux | |
| 5,084,023 | A | | 1/1992 | Lemieux | |
| 5,344,408 | A | | 9/1994 | Partika | |
| 5,419,766 | A | | 5/1995 | Chang et al. | |
| 5,501,675 | A | | 3/1996 | Erskine | |
| 5,575,777 | A | | 11/1996 | Cover et al. | |
| 5,700,250 | A | | 12/1997 | Erskine | |
| 5,702,367 | A | | 12/1997 | Cover | |

(Continued)

FOREIGN PATENT DOCUMENTS

| WO | 2014133617 A1 | 9/2014 |
| WO | 20160123620 A1 | 8/2016 |
| WO | 2017029361 A1 | 2/2017 |

OTHER PUBLICATIONS

Dual Protection Safety I.V. Catheter Supercath (TM) 5, a New Generation of Safety I.V. Catheter, www.medikit.co/jp/english/.

*Primary Examiner* — Manuel A Mendez
(74) *Attorney, Agent, or Firm* — Dickinson Wright PLLC

(57) ABSTRACT

A catheter assembly including a catheter carried by a catheter adapter, a needle having a sharp distal tip and disposed in the catheter such that in a first needle position, the needle extending beyond the catheter, a septum actuator having openings, the septum actuator disposed in the catheter adapter and configured to pierce a septum, and a spring clip disposed in the septum actuator and engaging the openings of the septum actuator in the first needle position.

18 Claims, 26 Drawing Sheets

(56) References Cited

U.S. PATENT DOCUMENTS

| | | |
|---|---|---|
| 5,797,880 A | 8/1998 | Erskine |
| 5,817,069 A | 10/1998 | Arnett |
| 5,967,490 A | 10/1999 | Pike |
| 6,090,078 A | 7/2000 | Erskine |
| 6,117,108 A | 9/2000 | Woehr et al. |
| 6,287,278 B1 * | 9/2001 | Woehr .............. A61M 25/0618 604/110 |
| 6,616,630 B1 | 9/2003 | Woehr et al. |
| 6,908,459 B2 | 6/2005 | Harding et al. |
| 7,214,208 B2 | 5/2007 | Vaillancourt |
| 8,048,036 B2 | 11/2011 | Woehr et al. |
| 8,226,612 B2 | 7/2012 | Nakajima |
| 8,257,313 B2 | 9/2012 | McKinnon et al. |
| 8,337,463 B2 | 12/2012 | Woehr et al. |
| 8,529,515 B2 | 9/2013 | Woehr et al. |
| 8,535,271 B2 | 9/2013 | Fuchs et al. |
| 8,936,575 B2 | 1/2015 | Moulton |
| 9,101,746 B2 | 8/2015 | Stout et al. |
| 9,381,324 B2 | 7/2016 | Fuchs et al. |
| 9,421,345 B2 | 8/2016 | Woehr et al. |
| 2005/0027263 A1 | 2/2005 | Woehr et al. |
| 2007/0255221 A1 | 11/2007 | Nakajima |
| 2012/0136311 A1 | 5/2012 | Knulsson et al. |
| 2012/0271235 A1 | 10/2012 | Fuchs |
| 2012/0277680 A1 | 11/2012 | Woehr et al. |
| 2013/0030391 A1 | 1/2013 | Baid |
| 2013/0178800 A1 | 7/2013 | Domonkos et al. |
| 2013/0184645 A1 | 7/2013 | Baid |
| 2013/0317426 A1 * | 11/2013 | Fiser ................. A61M 25/0618 604/110 |
| 2014/0094774 A1 | 4/2014 | Blanchard |
| 2014/0121604 A1 | 5/2014 | Knulsson et al. |
| 2017/0043135 A1 | 2/2017 | Knulsson |

* cited by examiner

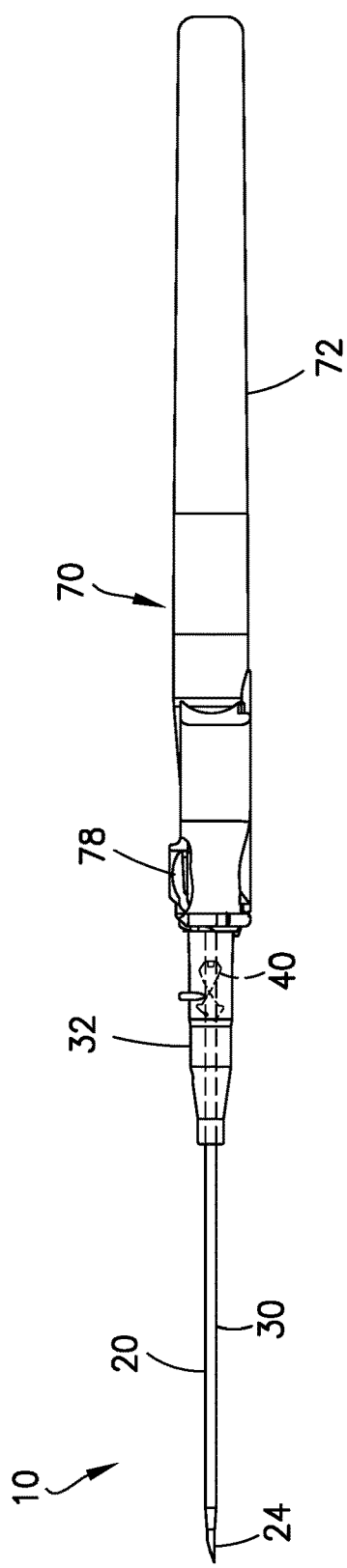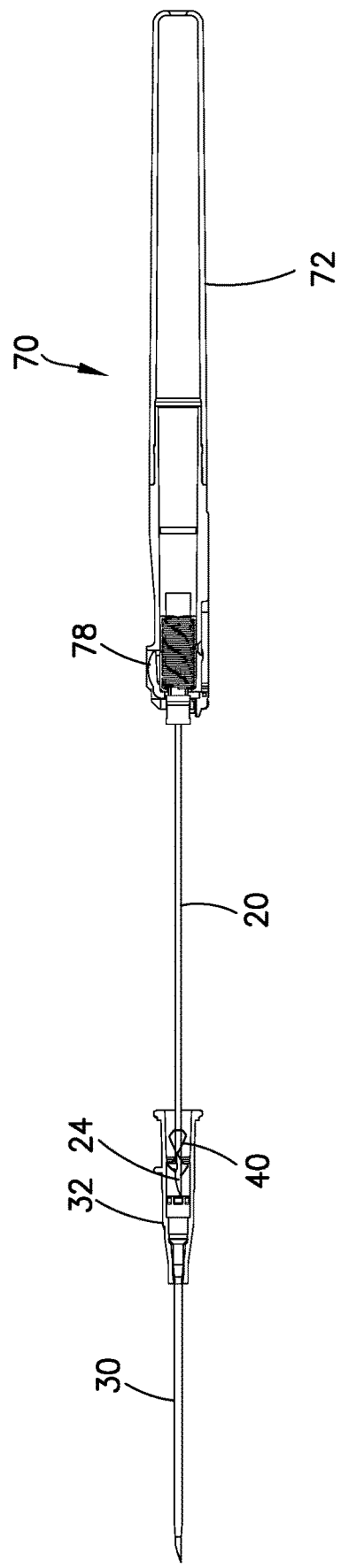
FIG.1
FIG.2

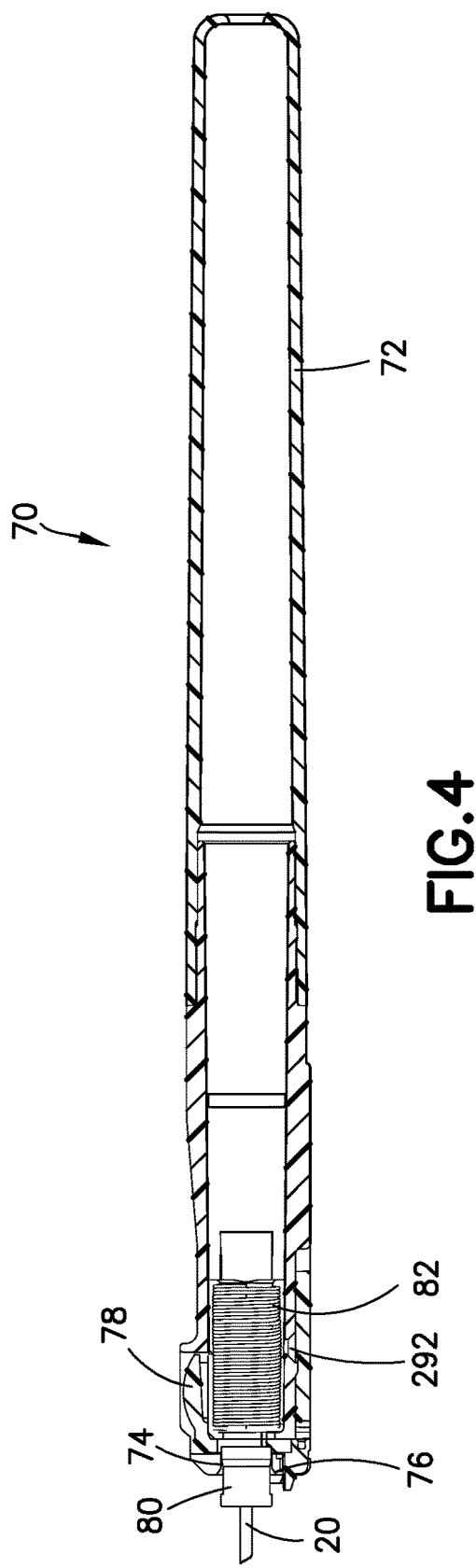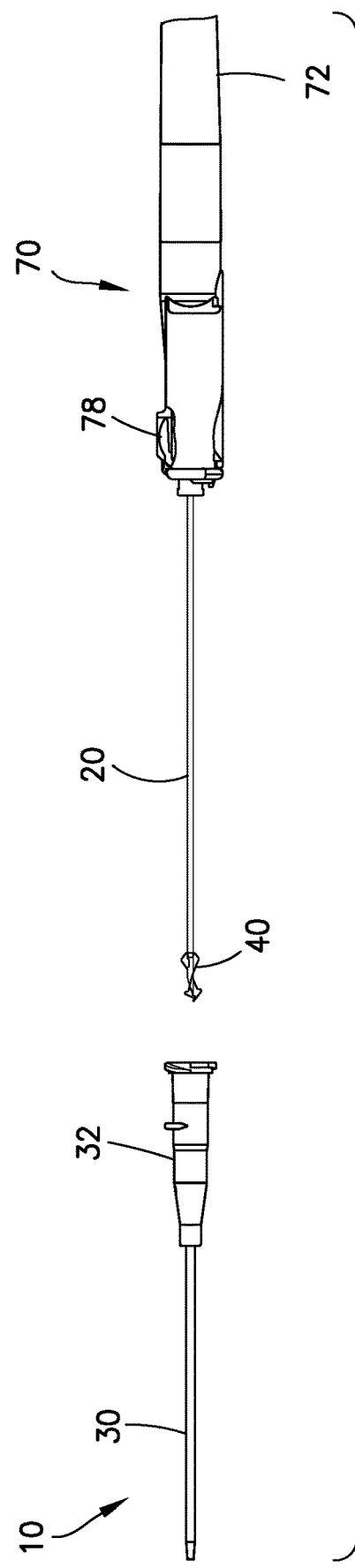

CATHETER ASSEMBLY

CROSS-REFERENCE

This application is a continuation of U.S. patent application Ser. No. 15/827,967 filed on Nov. 30, 2017, which discloses related subject matter in commonly assigned U.S. patent application Ser. No. 15/664,827, filed on Jul. 31, 2017, the entire disclosures of these applications being incorporated herein by reference.

FIELD

Various exemplary embodiments of the invention relate to needle protection and needle retraction in catheter assemblies.

BACKGROUND

Typical catheter assemblies incorporate one of two types of needle protection mechanisms. An active system is a needle protection mechanism that requires a separate user action to initiate needle protection, such as depression of an activation button to activate automatic and instantaneous needle retraction into a barrel assembly. This action can take place after the needle is withdrawn from a skin of a patient and from the catheter. Alternately, depression of the activation button can take place before the needle is withdrawn from the skin of the patient for safety reasons, to reduce blood splatter and/or contamination. On the other hand, a passive system is a needle protection mechanism that automatically protects the needle when a user manually retracts the needle from the catheter, typically using a spring clip and without requiring a separate user action. In other words, the needle is immediately protected when it is withdrawn from a skin of a patient and from the catheter.

Various disadvantages arise in each of the needle protection mechanisms. Specifically, in active systems, the user may neglect to depress the activation button or fail to perform the secondary user action to protect the needle. For example, when the activation button is not depressed, the used needle tip that is covered in blood is undesirably exposed from the body of a patient. In passive systems, the spring clip includes undesirable sharp edges, blood is exposed on the needle and the spring clip, and the spring clip can be manually manipulated to expose the distal tip of the needle after it is covered.

Additionally, blood control catheter assemblies have space requirements that invoke unique and creative design solutions to meet functional requirements within the restricted boundary.

SUMMARY OF THE INVENTION

It is an aspect of the present invention to provide a blood control catheter assembly where a spring clip is selectively engaged to a septum actuator during operation. Specifically, the spring clip includes flexible arms that are configured to enclose a distal end of the needle and simultaneously engage and disengage openings (flushing windows) in the septum actuator. The flexible arms include a cutout portion that allows the spring clip to engage and disengage with the openings of the septum actuator with minimal interference and improved compactness to meet size constraints. Alternately, the flexible arms can be narrow enough to allow the spring clip to engage and disengage with the openings of the septum actuator in a similar manner as described above. The spring clip is advantageously not engaged and does not contact the catheter adapter.

It is another aspect of the present invention to provide a blood control catheter assembly that incorporates both an active and passive system in a blood control catheter assembly. Such a catheter assembly remedies the disadvantages above and improves needle protection and needle retraction. Specifically, the needle tip is enclosed by a spring clip and the needle is retracted into the barrel assembly. In this manner, if the user forgets to press the activation button, the distal tip is already protected by the spring clip. When the activation button is depressed, the needle and the spring clip retract into the barrel assembly, thereby protecting the user from all hazards. Alternately, the needle and spring clip is retracted from the blood control catheter assembly manually by a user. Accordingly, the catheter assembly advantageously prevents needle re-exposure and reduces blood exposure.

The foregoing and/or other aspects of the present invention can be achieved by providing a catheter assembly including a catheter carried by a catheter adapter, a needle having a sharp distal tip and disposed in the catheter such that in a first needle position, the needle extending beyond the catheter, a septum actuator having openings, the septum actuator disposed in the catheter adapter and configured to pierce a septum and a spring clip disposed in the septum actuator and engages the openings in the first needle position.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 1 illustrates a side view of a first exemplary embodiment of a catheter assembly in a first needle position;

FIG. 2 illustrates a cross section view of the catheter assembly of FIG. 1 moving toward a second needle position;

FIG. 4 illustrates a partial cross section view of a barrel assembly of FIG. 2;

FIG. 6 illustrates a side view of the catheter assembly of FIG. 1 in a second needle position;

DETAILED DESCRIPTION OF EXEMPLARY EMBODIMENTS

Figure 3:
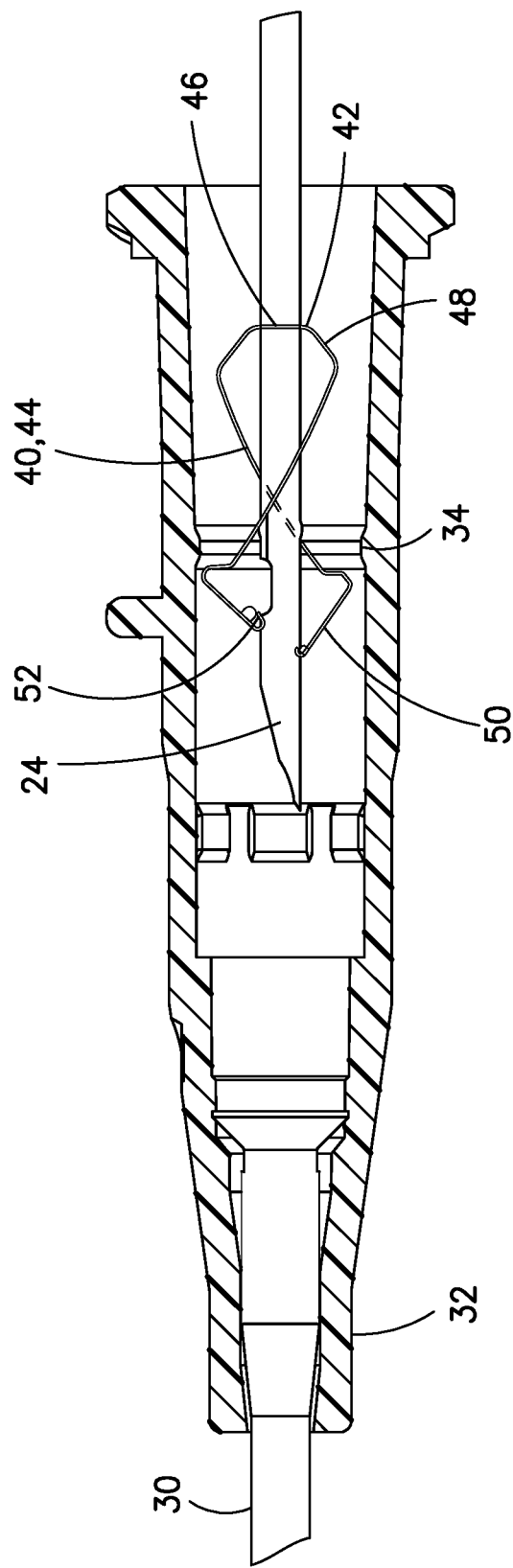
FIG. 3 illustrates a cross section view of a catheter adapter of FIG. 2.

FIGS. 1-9 illustrate a first exemplary embodiment of a catheter assembly 10. FIG. 1 illustrates the catheter assembly 10 in a first needle position ready for operation. According to one embodiment, the catheter assembly 10 includes a hollow introducer needle 20 having a sharp distal tip 24 for insertion in a skin of a patient. The needle 20 is disposed in a flexible catheter 30. The catheter 30 is used for medication delivery during use of the catheter assembly 10. In the first needle position, the sharp distal tip 24 of the needle 20 extends beyond the catheter 30 for insertion.

According to one embodiment, the catheter 30 and the needle 20 are carried or surrounded by a catheter adapter 32. FIG. 2 illustrates the needle 20 moving from the first needle position toward a second needle position after the user has placed the catheter 30 in the body of the patient and removed the needle 20 from the patient.

FIG. 3 illustrates, according to one embodiment, the catheter adapter 32 when the needle 20 is pulled back and approaching the second needle position. The catheter adapter 32 includes a retention feature 34 comprising a protrusion. The retention feature 34 retains a metal spring clip 40 when the spring clip 40 is in an open position as illustrated. Operation of the spring clip 40 is further described below.

The spring clip 40 is disposed in the catheter adapter 32 and cooperates with the needle 20 by selectively enclosing and locking the sharp distal tip 24 of the needle 20. Components and operation of the spring clip 40 are generally disclosed in U.S. Pat. No. 6,616,630, which is hereby incorporated by reference in its entirety.

Specifically, according to one embodiment, the spring clip 40 includes an opening 42 where the needle 20 passes through. One or more flexible arms 44 of the spring clip 40, preferably two flexible arms 44, engage and bias the needle 20 in the open position prior to the needle entering the second needle position. The flexible arms 44 apply a spring force to two sides of the needle 20. In the first needle position and prior to the second needle position, the spring clip 40 is open to allow the needle 20 to pass through.

At the distal end of the flexible arms 44 include distal walls 50. The distal walls 50 are angled walls have lips 52 at one end which contact the needle 20. The lips 52 are folded inward portions of distal walls 50 of the spring clip 40.

The spring clip 40 further includes a rear wall 46. The rear wall 46 is substantially perpendicular to a longitudinal axis of the needle 20 and connects the two flexible arms 44 to each other. The rear wall 46 also includes the opening 42 as described above. The rear wall 46 preferably includes a tapered outer surface 48. In another embodiment, the tapered outer surface 48 comprises a radius or a chamfer. As further described below, the tapered outer surface 48 advantageously provides guided movement of the spring clip 40 into a handle 71 and a barrel 72.

Figure 5:
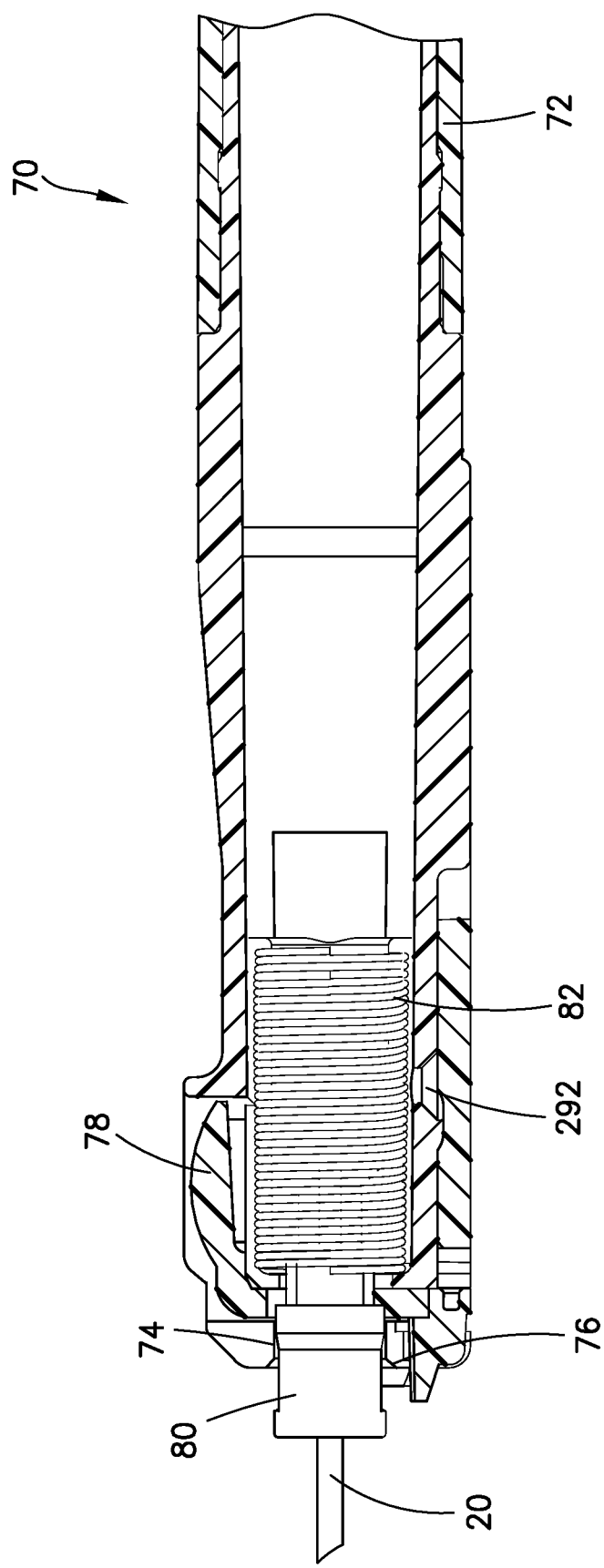
FIG. 5 illustrates a partial cross section view of a needle hub in the barrel assembly of FIG. 4.

FIGS. 4 and 5 illustrate the barrel assembly 70. According to one embodiment, the barrel assembly 70 includes the handle 71 (also referred to as a grip) and the barrel 72 (also referred to as barrel housing). The handle 71 includes an inner diameter 74 and a tapered inner surface 76 at a distal end of the handle 71. In another embodiment, the tapered inner surface 76 comprises a radius or a chamfer. In another embodiment, the tapered inner surface 76 connects and provides a transition between an outer surface of the handle 71 and an inner surface of the handle 71. A distal end of the barrel 72 is connected to a proximal end of the handle 71 during operation.

In this embodiment, the catheter assembly 10 includes both the tapered inner surface 76 at the distal end of the handle 71 and the tapered outer surface 48 of the spring clip 40. In an alternate embodiment, the catheter assembly 10 includes only the tapered inner surface 76 at the distal end of the handle 71. Likewise, in an alternate embodiment, the catheter assembly 10 includes only the tapered outer surface 48 of the spring clip 40. In another embodiment, the catheter assembly 10 does not include either of the tapered inner surface 76 at the distal end of the handle 71 or the tapered outer surface 48 of the spring clip 40.

The tapered inner surface 76 is configured to cooperate with the tapered outer surface 48 of the spring clip 40 to advantageously engage and guide the spring clip 40 into the handle 71 and the barrel 72. Also, the tapered outer surface 48 advantageously engages the tapered inner surface 76 to center the spring clip 40 with respect to the handle 71 and the barrel 72. The handle 71 and the barrel 72 houses the components of the barrel assembly 70 as further described below.

The barrel assembly 70 further includes a needle hub 80. The needle hub 80 is fixed to the needle 20 and moves within the handle 71 and the barrel 72. Specifically, the needle hub 80 is fixed adjacent to a proximal end of the needle 20. As illustrated in FIG. 1, the needle hub 80 is connected to the catheter adapter 32 when the needle 20 is in the first needle position. Movement of the needle hub 80 causes the needle to retract from the second needle position to a third needle position as described below.

The handle 71 and the barrel 72 also interacts with an activation button 78 to engage and release the needle hub 80 and a spring 82. Specifically, the spring 82 is disposed about the needle 20 and extending between the needle hub 80 and the proximal end of the barrel 72. The activation button 78 contacts the needle hub 80 while the spring 82 is compressed. When the activation button 78 is depressed, the needle hub 80 no longer contacts the activation button 78 and the spring 82 is subsequently released to move the needle hub 80 through the handle 71 and toward a proximal end of the barrel 72. That is, the activation button 78 is movably mounted adjacent to the distal end of the barrel 72 and adapted for selective engagement with the needle hub 80 to hold the needle hub 80 adjacent to the distal end of the barrel 72 against the bias of the spring 82. In the first needle position, the needle 20 extends beyond the distal end of the handle 71 and the barrel 72 and through the catheter 30 with the catheter hub 32 adjacent to the distal end of the barrel 72. Operation of the activation button 78 is described in U.S. Pat. Nos. 5,501,675 and 5,797,880, which are hereby incorporated by reference in their entirety. Further description of the operation is provided below.

According to one embodiment, FIG. 6 illustrates the catheter assembly 10 in the second needle position. In this position, the sharp distal tip 24 of the needle 20 is disposed in the spring clip 40 and shielded from an external environment. The user moving the needle 20 from the first needle position to the second needle position corresponds to a passive system. This is because the needle 20 is removed from the skin of the patient and the spring clip 40 protects the needle 20 in the same manual operation.

Figure 7:
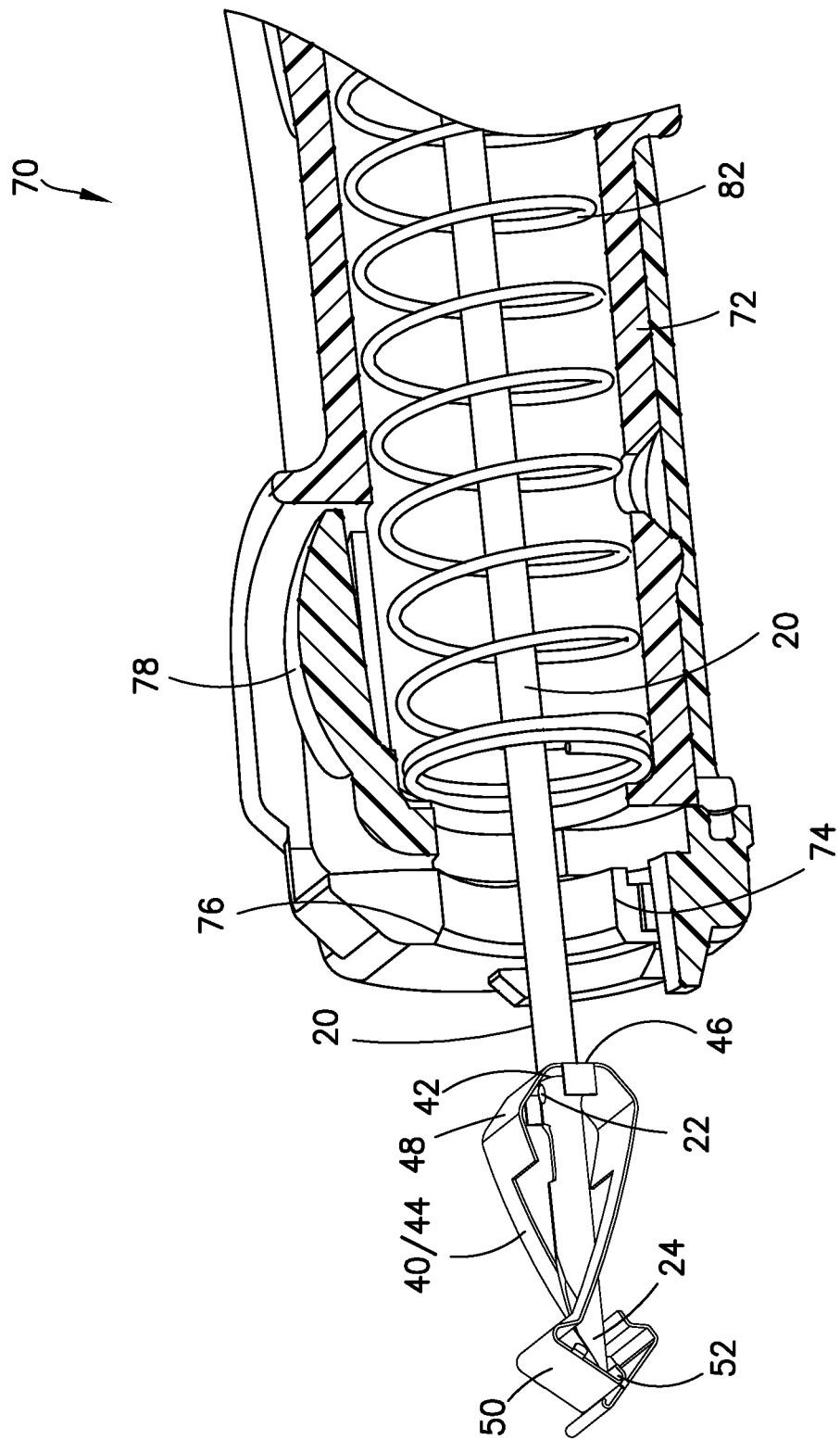
FIG. 7 illustrates a partial cross section view of the catheter assembly of FIG. 1 moving toward a third needle position.

As illustrated in FIG. 7, the spring clip 40 is in a closed position where the two flexible arms 44 bias against each other to enclose the sharp distal tip 24 of the needle 20. In another words, the distal walls 50 and the lips 52 overlap each other to close the spring clip 40 in a closed position. Specifically, the lip 52 of one flexible arm 44 contacts the distal wall 50 of the other flexible arm 44. The two flexible arms 44 of the spring clip 40 no longer bias the needle 20. Accordingly, the flexible arms 44 close the distal end of the spring clip 40 to prevent the needle 20 from exiting.

The needle 20 also includes a needle deformation 22 that provides the needle 20 with a local diameter that is larger than the diameter of the opening 42 in the spring clip 40. The needle deformation 22 prevents the needle 20 from exiting the spring clip 40 at its proximal end. Other means of retaining the sharp distal tip 24 inside the spring clip 40 includes the spring clip engaging a plate or a notch in the needle as described in U.S. Pat. No. 4,952,207, which is hereby incorporated by reference in its entirety.

When the spring clip 40 is disposed in the closed position, the spring clip 40 no longer engages the retention feature 34 of the catheter adapter 32. Thus, as illustrated in FIG. 6, the spring clip 40 is no longer retained in the catheter adapter 32 and is now able to be removed from the catheter adapter 32.

Figure 8:
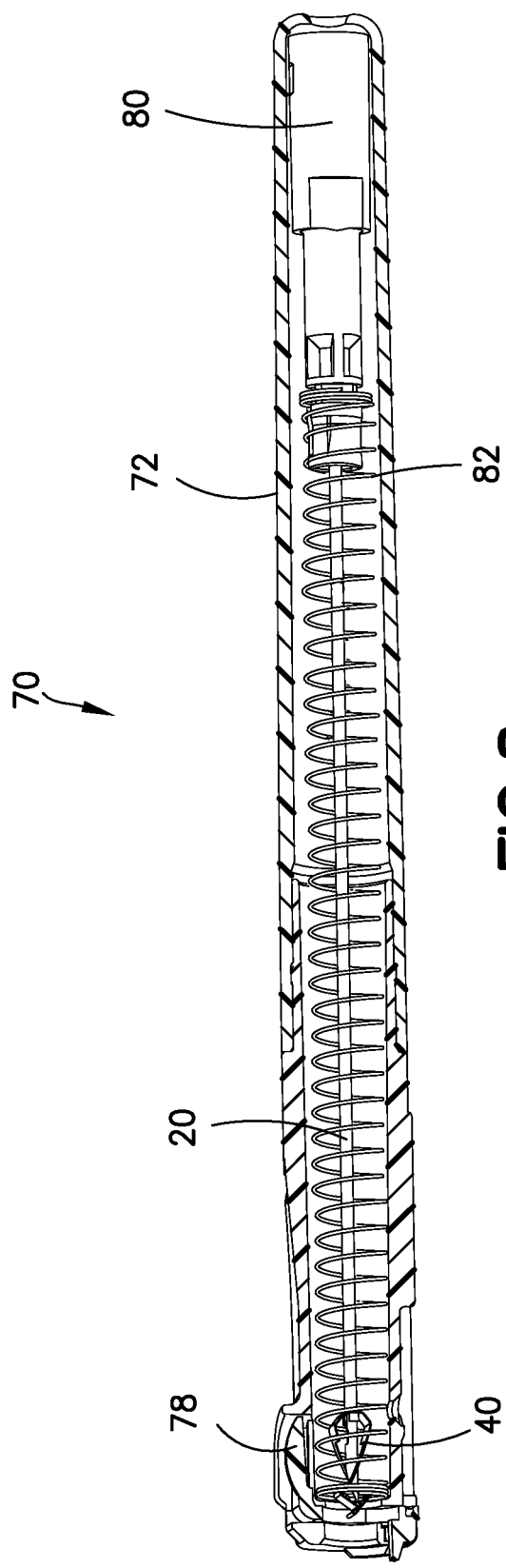
FIG. 8 illustrates a partial cross section view of the barrel assembly of FIG. 1 in the third needle position.

FIG. 8 illustrates, according to one embodiment, the barrel assembly 70 when the catheter assembly 10 is in the third needle position. As described above, when the activation button 78 is depressed, the spring 82 and the needle hub 80 are released and retracted to the proximal end of the barrel 72. That is, the activation button 78 triggers operational movement of the needle 20, the spring clip 40 and the needle hub 80 to be enclosed in the barrel 72. During this movement, the tapered inner surface 76 of the inner diameter 74 of the handle 71 cooperates with the tapered outer surface 48 of the spring clip 40 to advantageously engage and guide the spring clip 40 into the handle 71 and the barrel 72. Also, the tapered outer surface 48 engages the tapered inner surface 76 to advantageously center the spring clip 40 with respect to the handle 71 and the barrel 72.

Movement from the second needle position to the third needle position corresponds to an active system. This is because a secondary step subsequent to the initial withdrawal of the needle 20 from the skin of the patient takes place. Specifically, in this secondary step, the user depresses the activation button 78 causing the needle 20 to automatically retract via a spring force from the spring 82. Thus, in this third needle position, the sharp distal tip 24 and the spring clip 40 are safely enclosed in the barrel 72.

According to one embodiment, if the catheter 30 is inserted into the skin of a patient and the activation button 78 is depressed, the needle 20 and the needle hub 80 are immediately withdrawn into the barrel assembly 70. Under this scenario, the tip shielding of the second needle position automatically takes place. This movement corresponds to the passive system.

Typically, in the prior art, spring clips are not retracted into a barrel. Either spring clips are used to cover a sharp distal tip of a needle or a needle without a spring clip is retracted into the barrel. The catheter assembly 10 disclosed herein advantageously combines an active and a passive system to ensure increased safety to the user and reduces blood exposure and splatter. The catheter assembly 10 improves operation by providing the tapered inner surface 76 of the inner diameter 74 of the handle 71 to cooperate with the tapered outer surface 48 of the spring clip 40.

Figure 10:
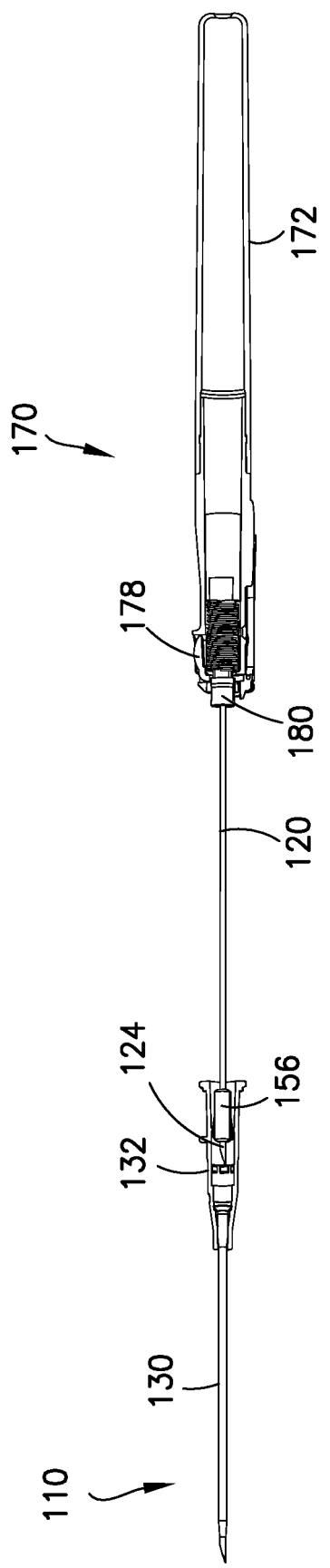
FIG. 10 illustrates a partial cross section view of a second exemplary embodiment of a catheter assembly moving toward a second needle position.
Figure 9:
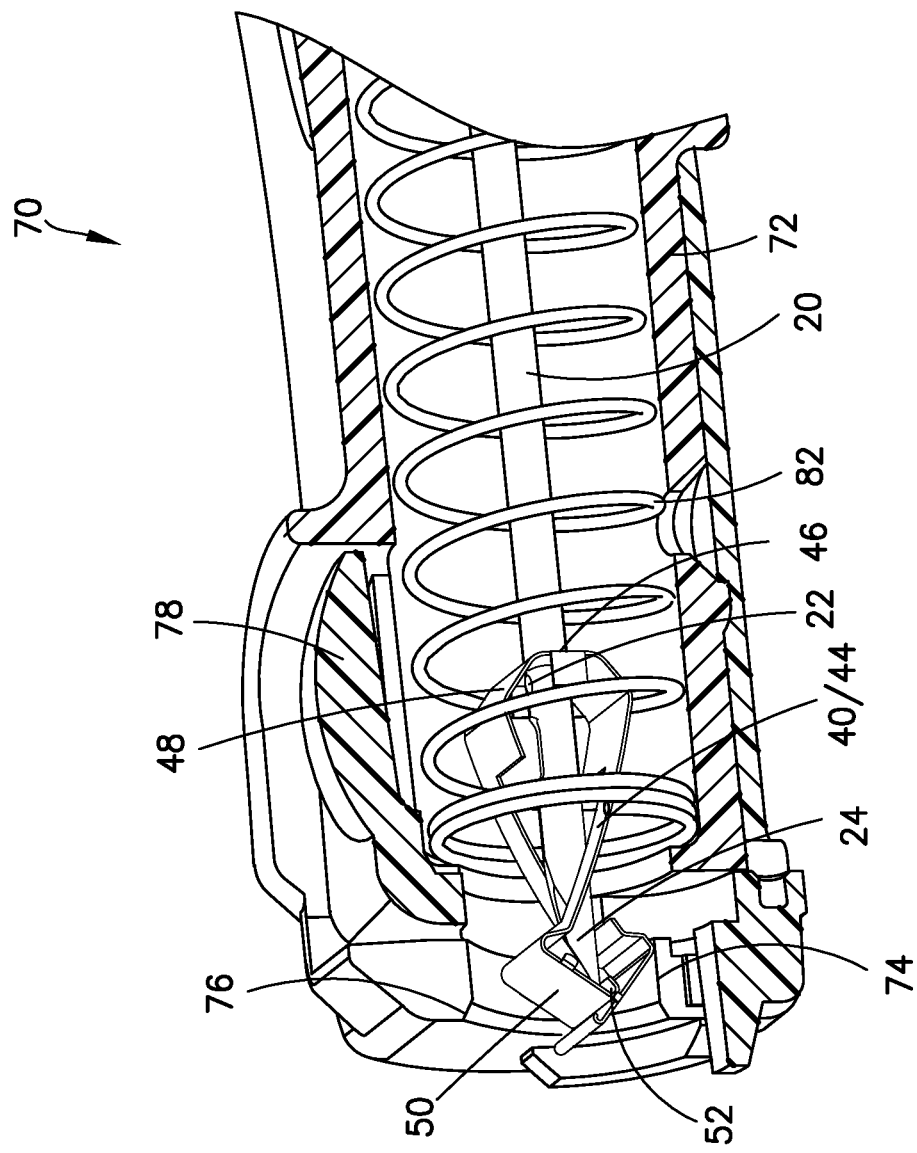
FIG. 9 illustrates a partial cross section view of a spring clip in the barrel assembly of FIG. 8.

FIGS. 10-19 illustrate a second exemplary embodiment of a catheter assembly 110. The catheter assembly 110 is a modified version of the catheter assembly 10 described above with the following differences. FIG. 10 illustrates the catheter assembly 110 when the user removes a needle 120 from a distal end of a catheter 130 and positions a sharp distal tip 124 of the needle 120 into a catheter adapter 132.

Figure 11:
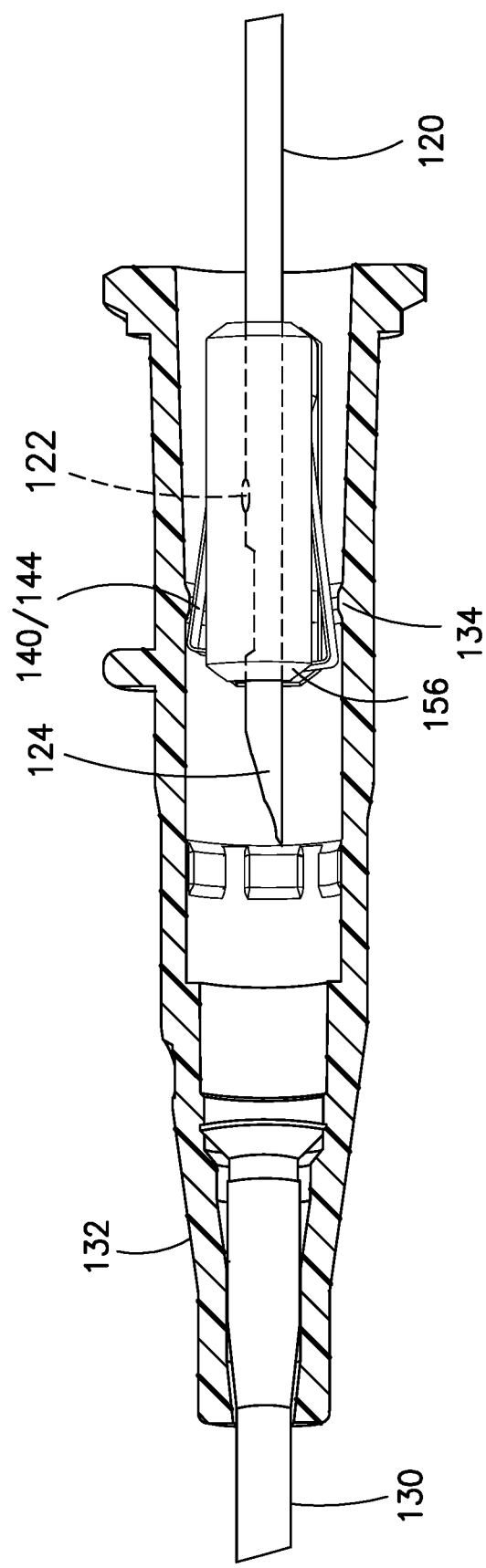
FIG. 11 illustrates a partial cross section view of a catheter adapter of FIG. 10.

FIG. 11 illustrates, according to one embodiment, the needle 120 inside the catheter adapter 132. As similarly described in the previous embodiment, a spring clip 140 selectively opens and closes to expose and enclose the sharp distal tip 124 of the needle 120. The spring clip 140 includes an opening 142 for the needle 120 to travel through. The spring clip 140 also includes a curved portion 154, distal walls 150 and lips 152 to enclose the sharp distal tip 124. The curved portion 154 is configured so that flexible arms 144 appropriately flex between open and closed positions of the spring clip 140. Additionally, the spring clip 140 includes a rear wall 146 and a tapered outer surface 148 at a proximal end of the spring clip 140. The catheter adapter 132 further includes a retention feature 134 that retains the spring clip 140 via the flexible arms 144 until the spring clip 140 is closed.

Figure 12:
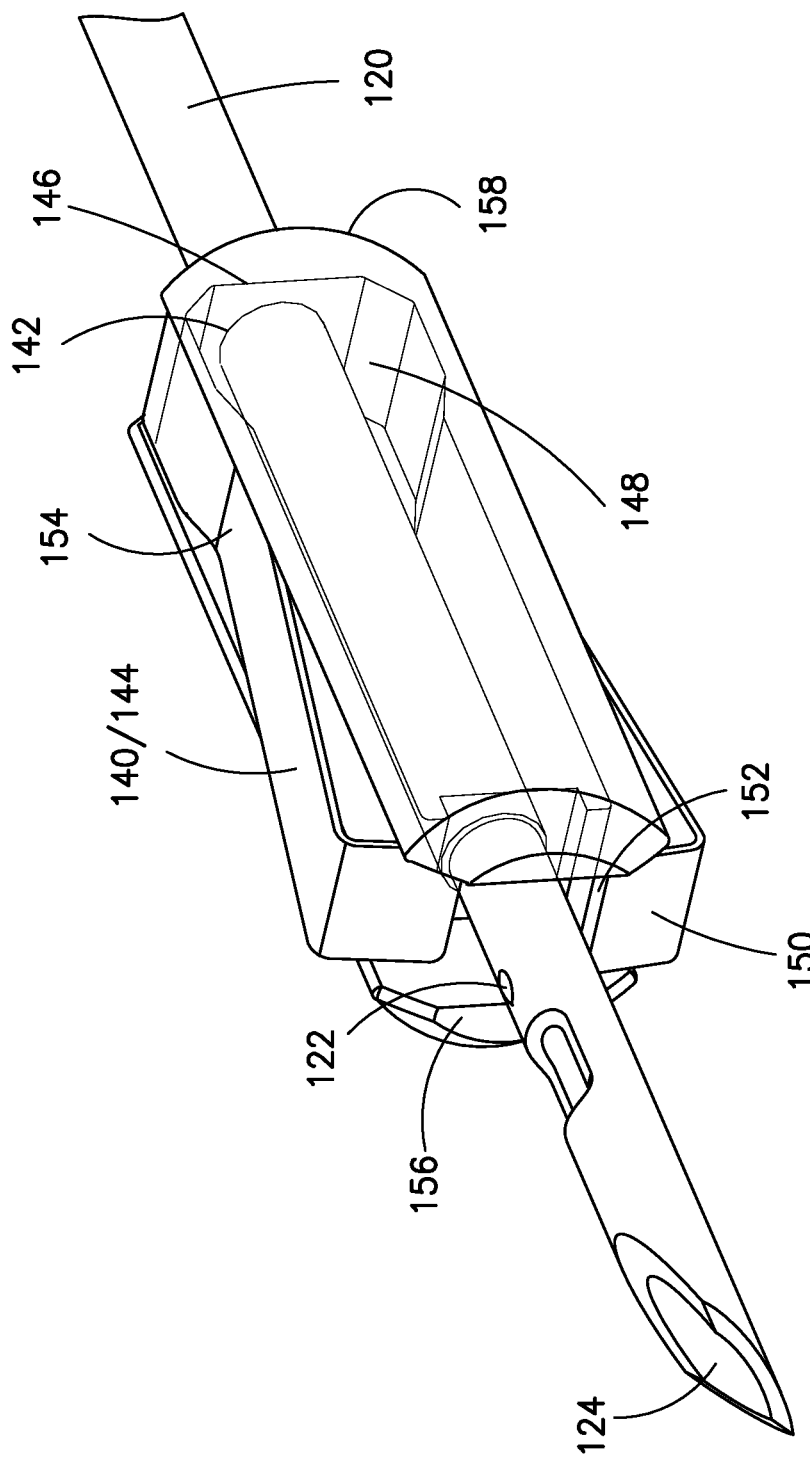
FIG. 12 illustrates a transparent perspective view of a spring clip and a clip housing of FIG. 11 moving toward a second needle position.

According to one embodiment, FIGS. 11 and 12 also illustrate a clip housing 156 that partially surrounds the spring clip 140. Features and operation of the clip housing 156 are similarly disclosed in U.S. patent application Ser. No. 15/481,166 filed on Apr. 6, 2017, which is hereby incorporated by reference in its entirety. Specifically, the clip housing 156 advantageously covers any sharp edges in the spring clip 140 to protect the user from inadvertent contact. The clip housing 156 also includes locking and/or engagement features to prevent inadvertent separation from the spring clip 140.

The flexible arms 144 of the spring clip 140 extend outside of the clip housing 156 in the open position of the spring clip 140. The clip housing 156 of this embodiment also advantageously includes a tapered outer surface 158 at a distal end of the clip housing 156. In another embodiment, the tapered outer surface 158 comprises a radius or a chamfer. The tapered outer surface 158 is configured to advantageously provide guided movement of the clip housing 156 into a handle 171 and a barrel 172 as further described below and as similarly described in the previous embodiment. Also, the tapered outer surface 158 advantageously centers the spring clip 140 with respect to the handle 171 and the barrel 172. Accordingly, the tapered outer surface 158 of the clip housing 156 cooperates with the tapered outer surface 148 at the rear wall 146 of the spring clip 140 to advantageously provide smooth travel into the handle 171 and the barrel 172.

Figure 13:
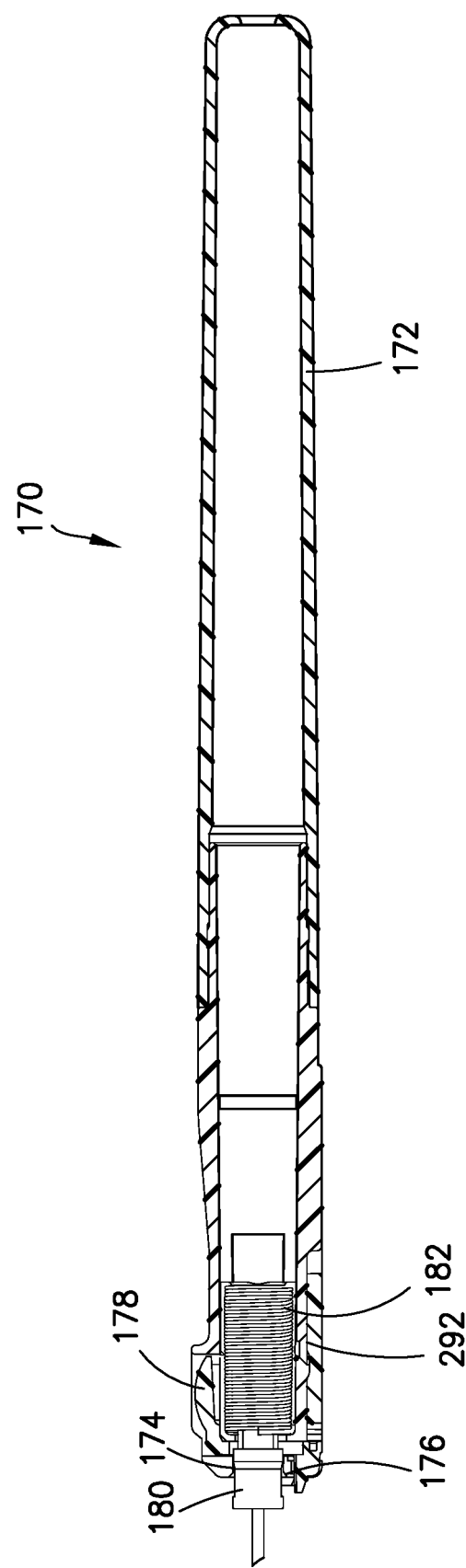
FIG. 13 illustrates a partial cross section view of a barrel assembly of FIG. 10.
Figure 14:
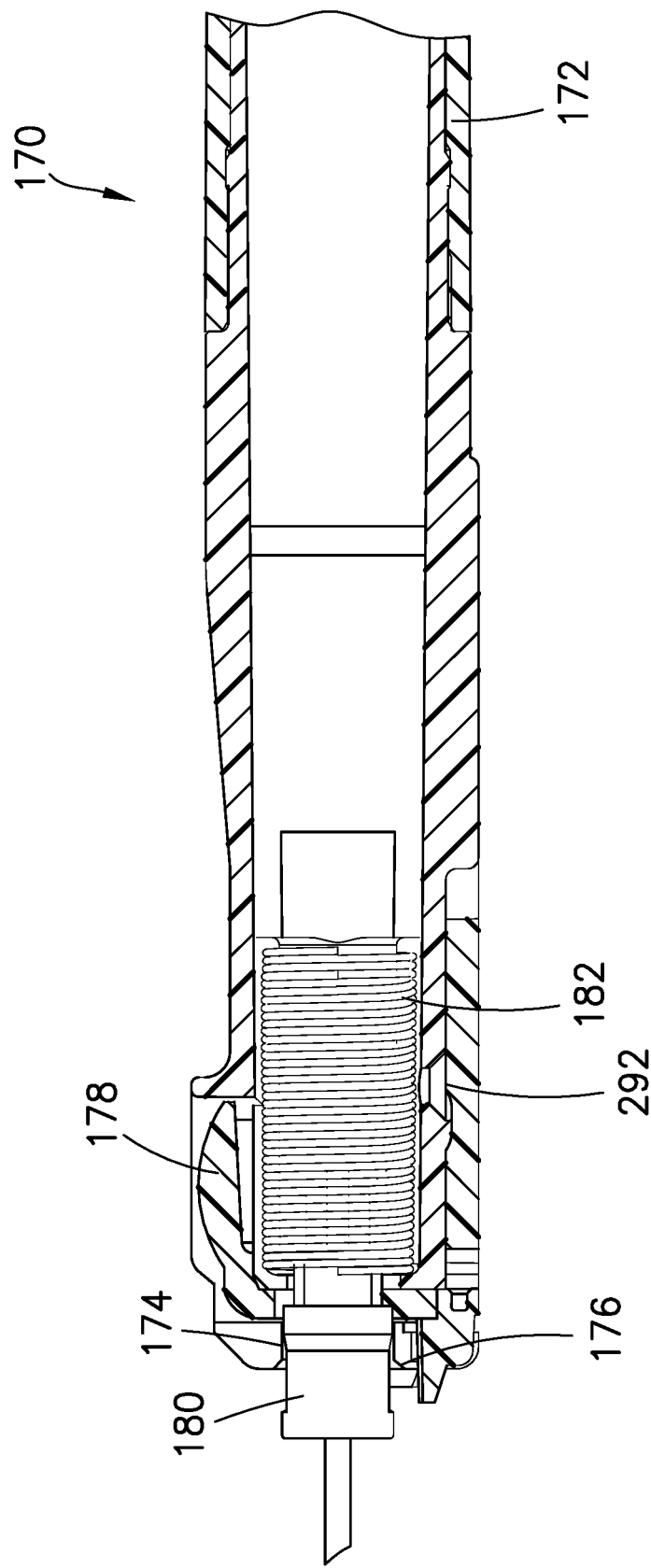
FIG. 14 illustrates a partial cross section view of a needle hub in the barrel assembly of FIG. 13.

According to one embodiment, FIGS. 13 and 14 illustrate a barrel assembly 170. As similarly described in the previous embodiment, the barrel assembly 170 includes the handle 171 having an inner diameter 174. The inner diameter 174 includes a tapered inner surface 176 disposed at a distal end of the handle 171. The tapered inner surface 176 of the inner diameter 174 of the handle 171 cooperates with the tapered outer surface 148 of the spring clip 140 and the tapered outer surface 158 of the clip housing 156 to advantageously engage and guide the spring clip 140 and the clip housing 156 into the handle 171 and the barrel 172. Also, the tapered outer surface 148 of the spring clip 140 and the tapered outer surface 158 of the clip housing 156 engage the tapered inner surface 176 to advantageously center the spring clip 140 and the clip housing 156 with respect to the handle 171 and the barrel 172.

As similarly described in the previous embodiment, the barrel assembly 170 further includes an activation button 178 and a spring 182 that cooperates with a needle hub 180 for retraction. The needle 120 is fixed to the needle hub 180 so that the needle 120 is retracted into the barrel 172 when the activation button 178 is depressed.

Figure 15:
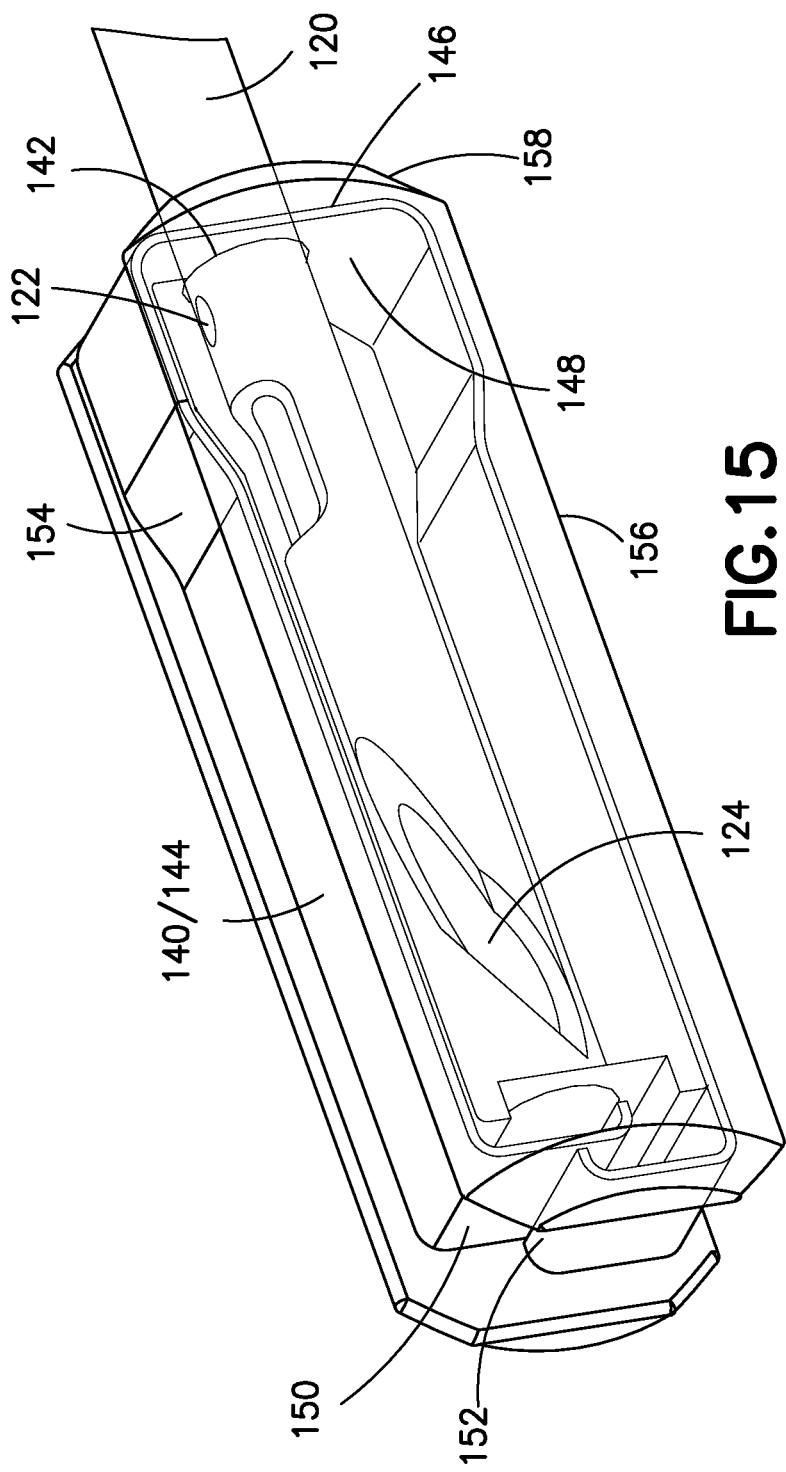
FIG. 15 illustrates a transparent perspective view of the spring clip and the clip housing of FIG. 10 in the second needle position.

FIG. 15 illustrates, according to one embodiment, the spring clip 140 being substantially disposed in the clip housing 156 and in a closed position where the needle is in a second needle position. Specifically, the distal walls 150 are offset and the lip 152 of one of the distal walls 150 contacts the other distal wall 150 to block the distal tip 124 of the needle 120 from exiting the clip housing 156. Also, after the spring clip 140 is in the closed position, a distal portion of the spring clip 140 may extend beyond the clip housing 156.

Figure 16:
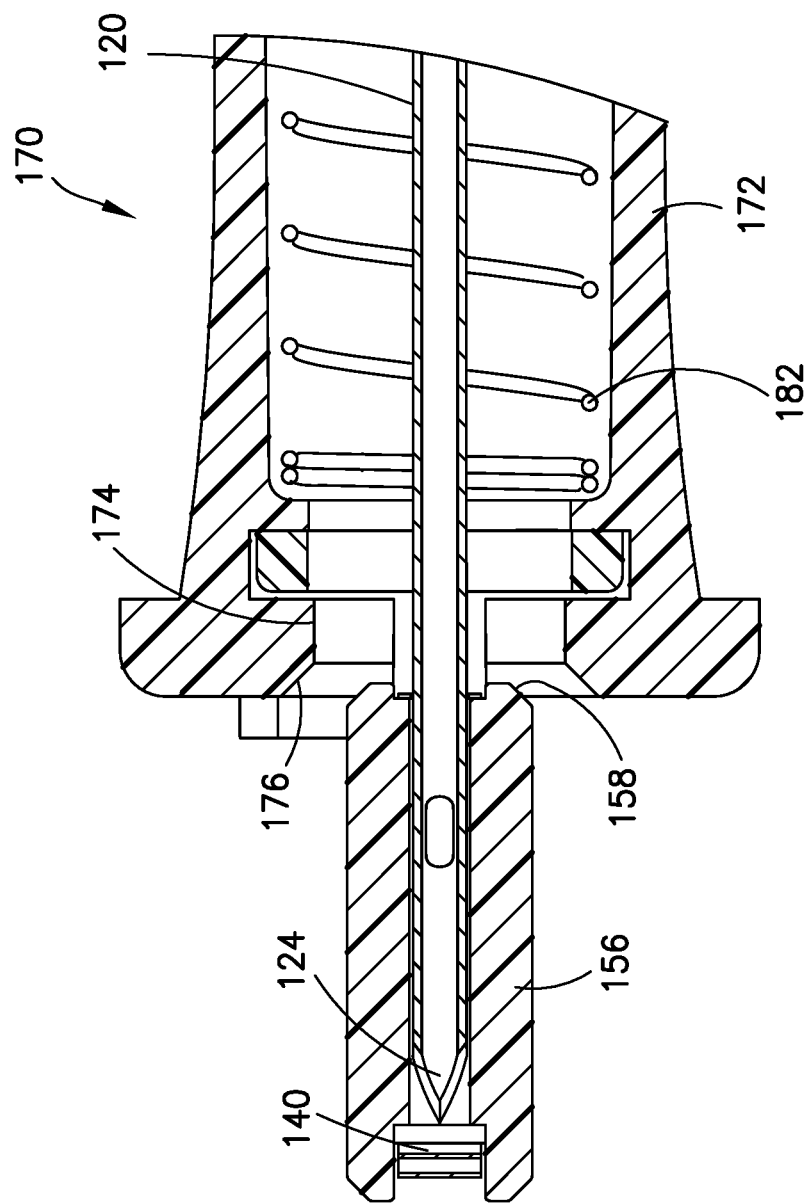
FIG. 16 illustrates a top section view of the spring clip, clip housing and barrel assembly of FIG. 10 in the second needle position.
Figure 17:
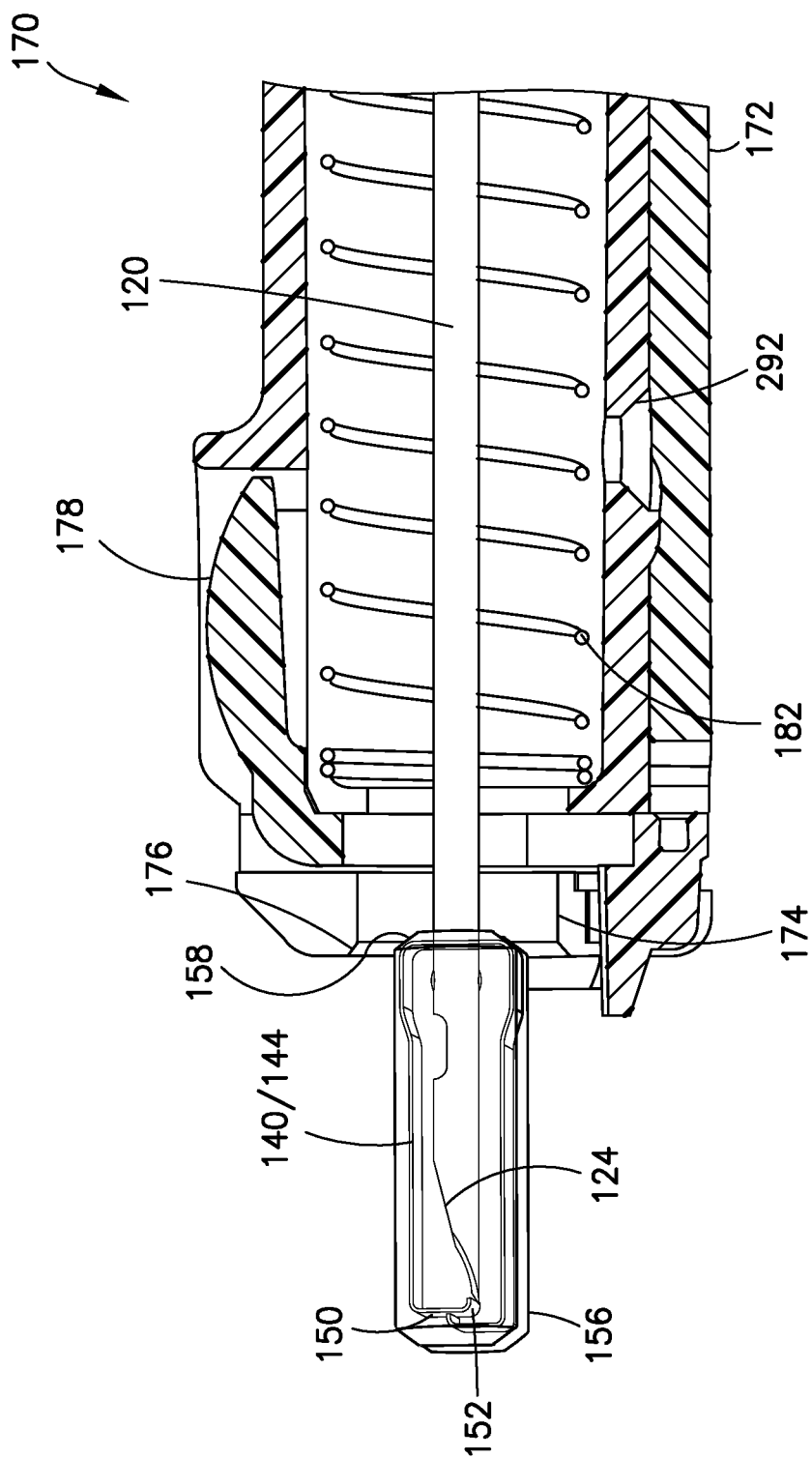
FIG. 17 illustrates a transparent cross section view of the spring clip, clip housing and the barrel assembly of FIG. 10 in the second needle position.

According to one embodiment, FIG. 16 illustrates a top section view and FIG. 17 illustrates a cross section view of the spring clip 140 and the clip housing 156. Both of these figures illustrate the spring clip 140 and the clip housing 156 being retracted into the barrel 172 from the second needle position to a third needle position.

Figure 18:
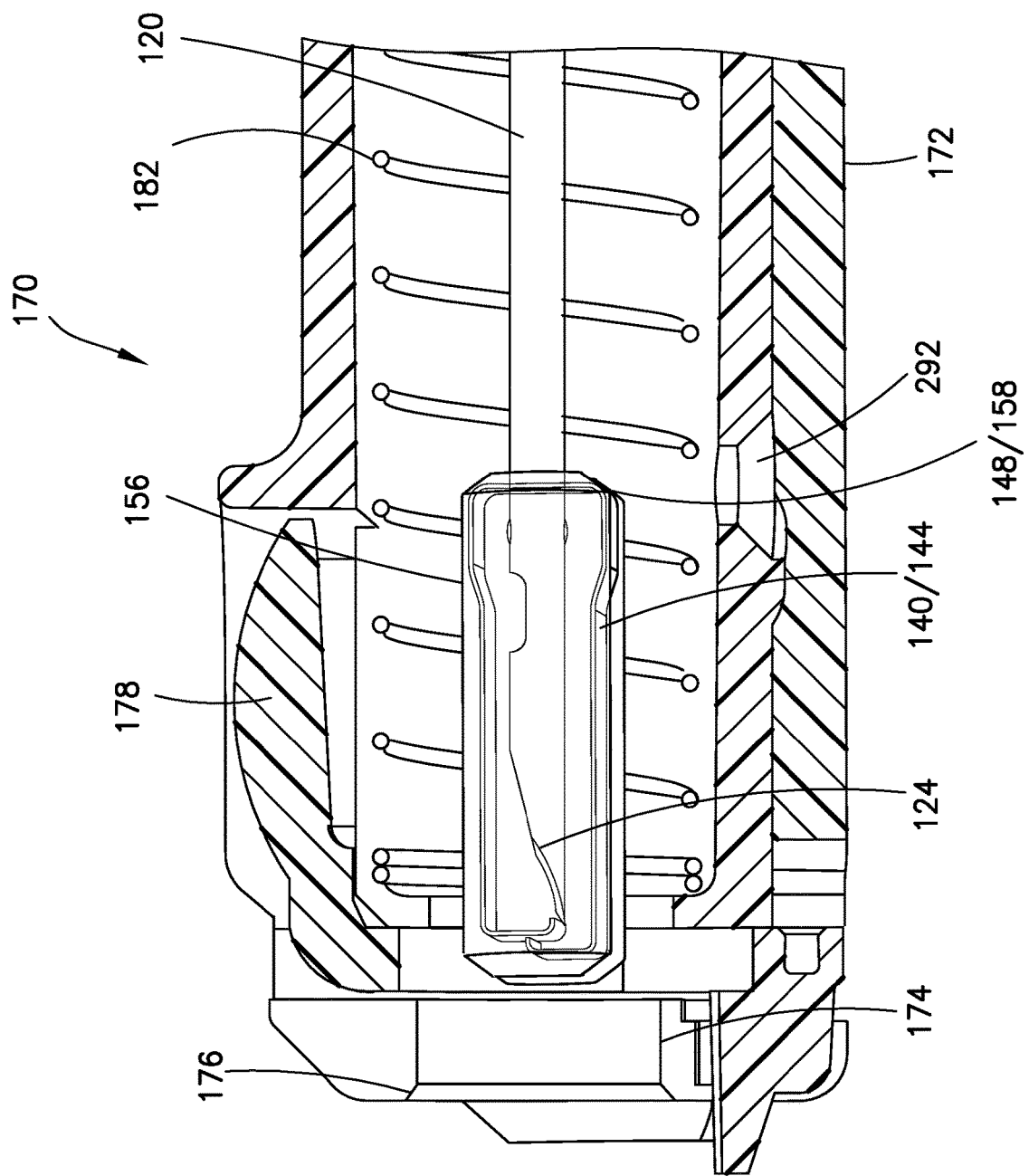
FIG. 18 illustrates a transparent cross section view of the spring clip, clip housing and the barrel assembly of FIG. 10 in a third needle position.
Figure 19:
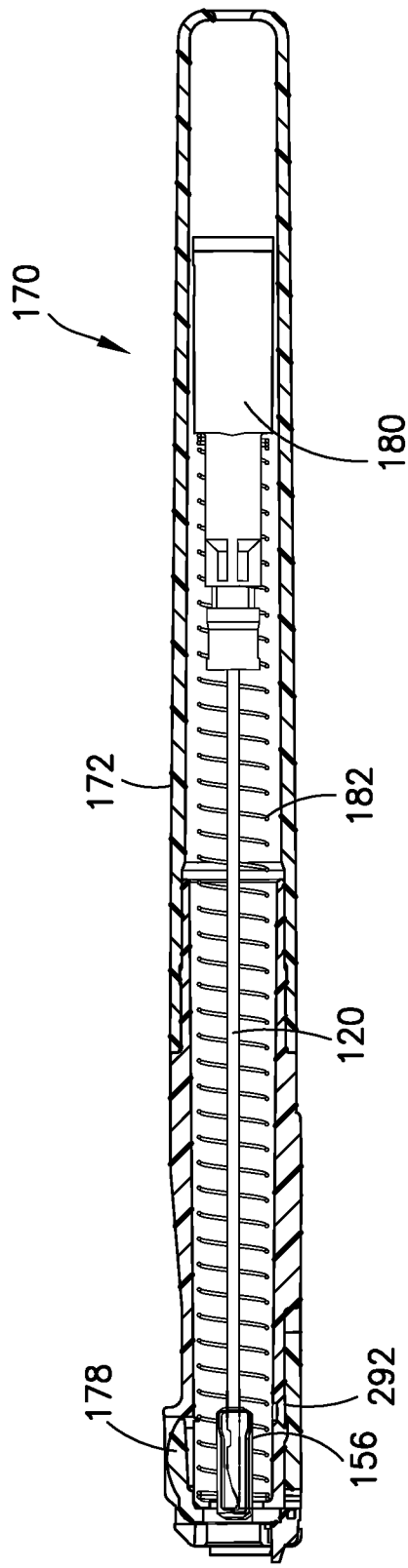
FIG. 19 illustrates a partial cross section view of the barrel assembly of FIG. 10 in the third needle position.

As similarly described in the previous embodiment, FIGS. 18 and 19 illustrate the spring clip 140 and the clip housing 156 in the barrel 172. This is the third needle position of the needle 120 of the catheter assembly 110.

Figure 20:
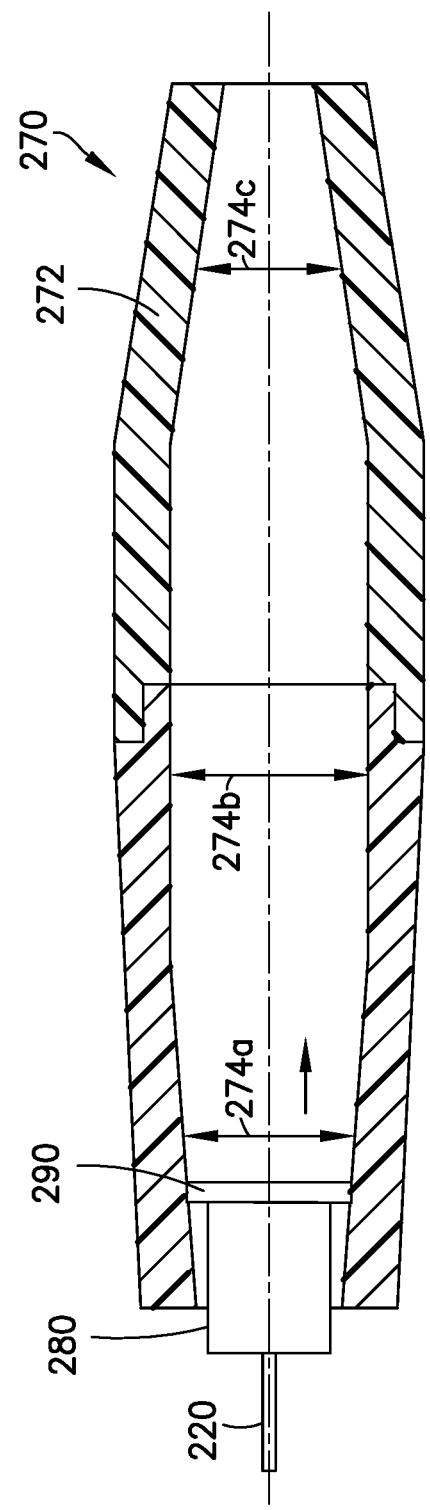
FIG. 20 illustrates a cross section view of a third exemplary embodiment of a barrel assembly with a needle hub in a starting position.
Figure 21:
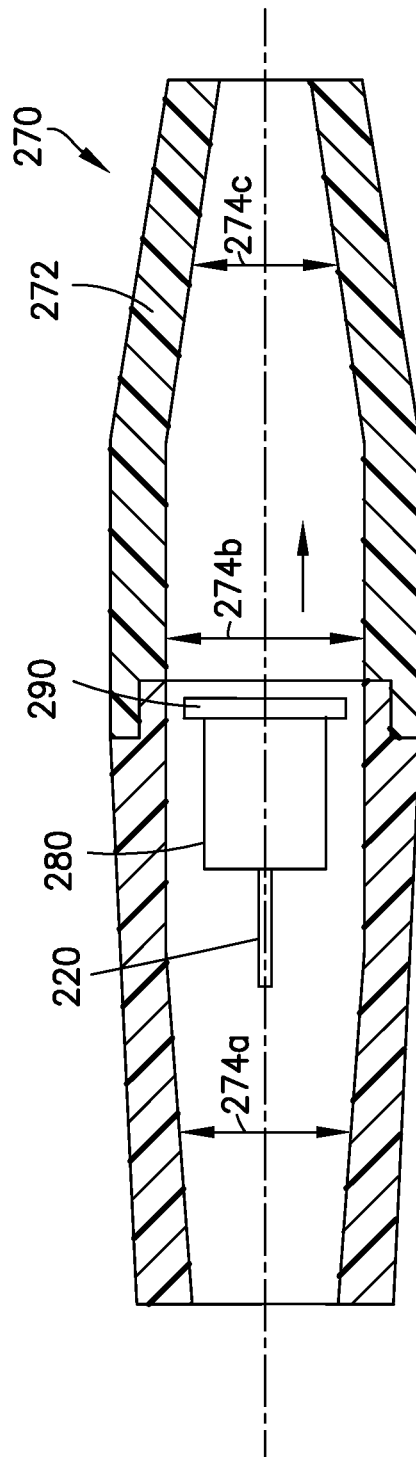
FIG. 21 illustrates a cross section view of the barrel assembly of FIG. 20 with the needle hub in an intermediate position.
Figure 22:
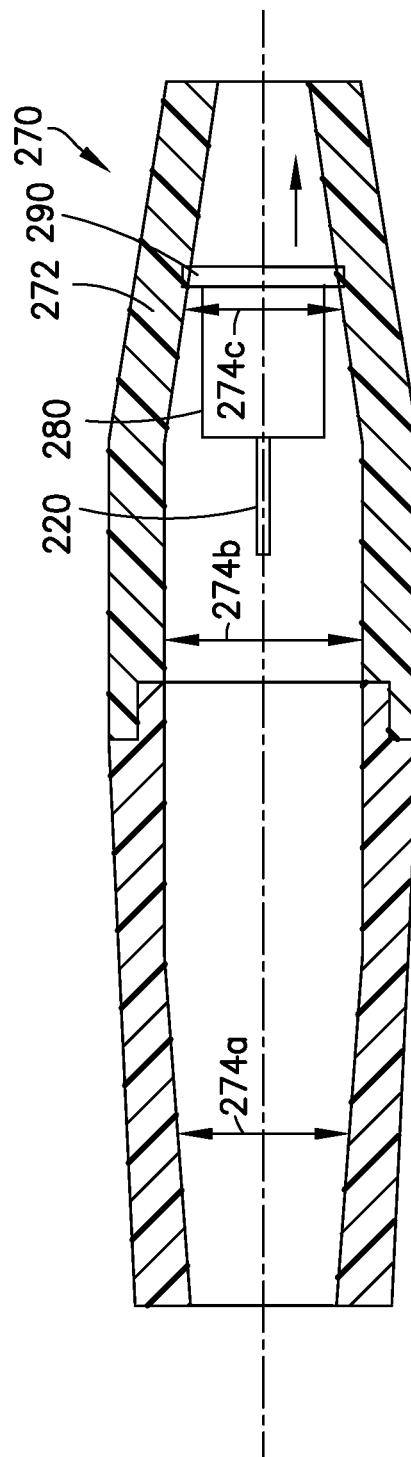
FIG. 22 illustrates a cross section view of the barrel assembly of FIG. 20 with the needle hub in an end position.

FIGS. 20-22 illustrate a third exemplary embodiment of a barrel assembly 270. The barrel assembly 270 is a modified version of the barrel assembly 70, 170 described above with the following improvements to control a retraction speed of a needle 220 in a handle 271 and a barrel 272.

In the previous embodiments described above, when the activation button 78, 178 is depressed, the needle hub 80, 180 is retracted into the handle 71, 171 and the barrel 72, 172 via force from the spring 82, 182. However, the retraction speed of the needle hub 80, 180 may be high, which can cause blood to splatter during retraction. Various damping mechanisms have been used in the prior art including a silicone gel, bladder air vents, O-rings, a crushable filter and spring compression nodes as described in U.S. Pat. Nos. 5,575,777, 5,702,367 and 6,090,078, which are hereby incorporated by reference in their entirety.

According to one embodiment, the barrel assembly 270 provides a controlled variable retraction speed of the needle 220 into the handle 271 and the barrel 272 of the catheter assembly. Specifically, the handle 271 includes a first inner diameter 274a, a second inner diameter 274b and a third inner diameter 274c. The first inner diameter 274a and the third inner diameter 274c are substantially similar. Also, the second inner diameter 274b is greater than each of the first inner diameter 274a and the third inner diameter 274c, respectively. The three inner diameters 274a, 274b, 274c are connected via inner diameter tapers to provide a continuous changing inner diameter.

The barrel assembly 270 further includes a needle hub 280 that secures the needle 220. A first damping mechanism 290 is advantageously fixed to a proximal end of the needle hub 280. In one embodiment, the first damping mechanism 290 is a silicone washer or a silicone disc.

In operation of the catheter assembly, when the activation button 78, 178 is depressed, an outer diameter of the first damping mechanism 290 is in frictional contact with the first inner diameter 274a. This is because the first inner diameter 274a is smaller than the outer diameter of the first damping mechanism 290. As a result, the needle hub 280 and needle 220 advantageously begin to move slowly into the handle 271 and the barrel 272.

As the needle hub 280 continues to move in the handle 271 and the barrel 272, the inner diameter increases in size to the second inner diameter 274b. The second inner diameter 274b is larger than the outer diameter of the first damping mechanism 290. Accordingly, there is clearance (significantly reduced frictional contact) between the second inner diameter 274b and the first damping mechanism 290. As a result, the needle hub 280 advantageously picks up speed and moves faster through the handle 271 and the barrel 272.

As the needle hub 280 approaches the end of its travel in the barrel 272, the inner diameter of the barrel 272 decreases in size to the third inner diameter 274c. The outer diameter of the first damping mechanism 290 is in frictional contact with the third inner diameter 274c. This is because the third inner diameter 274c is smaller than the outer diameter of the first damping mechanism 290. As a result, the needle hub 280 advantageously slows down in speed as it approaches the end of travel in the barrel 272.

The catheter assembly incorporating the barrel assembly 270 of this embodiment advantageously provides slow needle retraction at the beginning and at the end of the needle travel to reduce blood splatter and provide smooth movement of the needle 220 and needle hub 280 during retraction. The changing diameters in the handle 271 and the barrel 272 advantageously provide a speed damping profile to control the speed of the needle retraction at various positions.

The speed damping profile can be adjusted based on the desired retraction speed of the needle 220 and the needle hub 280. According to one embodiment, the third inner diameter 274c is smaller than the first inner diameter 274a to advantageously provide a slower retraction speed at the end of travel compared to at the beginning of travel. According to another embodiment, the first inner diameter 274a is smaller than the third inner diameter 274c to advantageously provide a slower retraction speed at the beginning of travel compared to at the end of travel. According to one embodiment, the second inner diameter 274b is substantially similar to the first and third inner diameters 274a, 274c to advantageously provide a slow retraction speed of the needle 220 and needle hub 280 throughout travel in the handle 271 and the barrel 272.

According to one embodiment, the width of each of the inner diameters 274a, 274b, 274c are varied to adjust the speed damping profile. Specifically, the width of the inner diameters 274a, 274b, 274c advantageously control an amount of time for retraction at each portion of the handle 271 and the barrel 272 as the needle 220 and the needle hub 280 travel through the handle 271 and the barrel 272. The amount of friction between the inner diameters 274a, 274b, 274c and the first damping mechanism 290 (how much interference is present), as well as the strength of the spring 82, 182 also advantageously controls the amount of time for retraction at each portion of the handle 271 and the barrel 272.

A fourth exemplary embodiment of a catheter assembly is a modified version of the barrel assembly 270 described above with the following differences. Specifically, the handle 271 and the barrel 272 include a first and second inner diameter 274a, 274b as similarly described above. The barrel assembly 270 also includes a first damping mechanism 290 being fixed at a proximal end of a needle hub 280. The barrel assembly 270 further includes a second damping mechanism 291. The first damping mechanism 290 is a silicone washer as similarly described above and the second damping mechanism 291 is a silicone gel. The silicone gel 291 is applied at a proximal end of the spring 82, 182 prior to retraction. FIGS. 4, 5, 13, 14, 17-19 illustrate an exemplary access hole 292 that is provided in the handle 71, 171 for the user to supply the silicone gel 291.

In operation of the catheter assembly with the barrel assembly 270 of this embodiment, when the activation button 78, 178 is depressed, an outer diameter of the first damping mechanism 290 is in frictional contact with the first inner diameter 274a. This is because the first inner diameter 274a is smaller than the outer diameter of the first damping mechanism 290. As a result, the needle hub 280 and needle 220 advantageously begin to move slowly into the handle 271 and the barrel 272 during retraction.

As the needle hub 280 continues to move in the handle 271 and the barrel 272, the inner diameter of the handle 271 and the barrel 272 increases to the second inner diameter 274b. The second inner diameter 274b is larger than the outer diameter of the first damping mechanism 290. Accordingly, there is significantly less frictional contact between the second inner diameter 274b and the first damping mechanism 290. As a result, the needle hub 280 advantageously picks up speed and moves faster through the handle 271 and the barrel 272 during retraction.

As the needle hub 280 approaches the end of its travel in the barrel 272, the spring 82, 182 advantageously begins to move through the applied silicone gel of the second damping mechanism 291. The silicone gel of the second damping mechanism 291 resists the extension of the spring 82, 182 to advantageously slow the retraction of the needle 220 and the needle hub 280. Accordingly, the combination of the first and second damping mechanisms 290, 291 advantageously provides a similar speed damping profile during needle retraction as the third embodiment described above.

This configuration advantageously reduces the manufacturing complexities of more than two controlled inner diameters in the handle 271 and the barrel 272. Also, the combination of the silicone washer 290 and the silicone gel 291 advantageously provide similar damping characteristics while reducing blood splatter and provides smooth movement of the needle 220 and the needle hub 280 during retraction.

According to one embodiment, the silicone gel of the second damping mechanism 291 is applied to the distal end of the spring 82, 182, as well as the proximal end of the inner diameter of the handle 271. In this manner, the silicone gel 291 is in contact with the spring 82, 182 in the compressed state, as well as when the spring 82, 182 moves to its extended state. Accordingly, the silicone gel 291 resists the extension of springs 82, 182 while contacting the needle hub 280 to slow its movement throughout travel. Applying silicone gel 291 in this manner advantageously allows coils of the springs 82, 182 to expand one at a time, instead of all at once.

Such a configuration advantageously improves the accuracy of the speed damping profile during needle retraction, particularly at the beginning of travel by slowly permitting the initial movement of the needle hub 280 after initial activation. This configuration also advantageously avoids the use of a silicone washer 290, which is susceptible to providing excessive friction upon activation. Under this scenario, the frictional force is greater than the spring force and thus, the needle 220 does not retract and remains in an unsafe condition. Accordingly, the silicone gel 291 advantageously provides a strong solution for the initial, activation phase.

According to one embodiment, the silicone gel 291 is provided to the distal end of the spring 82, 182 in the compressed state and the silicone washer 290 is fixed to the proximal end of the needle hub 280. The silicone washer 290 only significantly contacts the inner diameter of the barrel 272 near the end of travel to provide a significant frictional force. In this manner, the silicone gel 291 advantageously provides a strong solution for the initial, activation phase, as similarly described above, while the silicone washer 290 provides a better slow/speed reduction solution at the end of travel. Using the silicone washer 290 at the end of travel instead of silicone gel 291 advantageously avoids the needle hub 280 from simply "crashing" into a pile of silicone gel 291 at the end and provides better speed reduction.

In another embodiment, the silicone washer as the first damping mechanism 290 is disposed at the proximal end of the needle hub 280 and the silicone gel as the second damping mechanism 291 is disposed at the proximal end of the inner diameter of the barrel 272. The silicone washer interacts with the inner diameter of the handle 271 and the barrel 272 to control initial retraction of the needle hub 280 as similarly described above. The silicone gel at the proximal end of the inner diameter of the barrel 272 contacts the needle hub 280 to slow the end of travel in the barrel 272. Such a configuration advantageously provides another way to control the speed damping profile during needle retraction.

In another embodiment, the silicone gel as the second damping mechanism 291 is disposed at the proximal end of the needle hub 280, applied to the spring 82, 182 and disposed at the proximal end of the inner diameter of the barrel 272. The silicone gel at the proximal end of the needle hub 280 contacts the inner diameter of the handle 271 to slow the retraction speed. A similar effect happens with the silicone gel 291 at the proximal end of the inner diameter of the barrel 272 as the needle hub 280 approaches the end of travel in the barrel 272. However, at the proximal end of the inner diameter of the barrel 272, the spring also mixes with the residual silicone gel from the proximal end of the needle hub 280 to provide further damping of the retraction speed.

In this manner, the silicone gel 291 advantageously slows retraction of the needle hub 280 at the end to obtain a smoother deceleration and stoppage of the needle hub 280 in the retracted position. Such a configuration advantageously provides another way to control the speed damping profile during needle retraction while only using silicone gel. In another embodiment, access holes 292 are advantageously provided near any one of the proximal end of the spring 82, 182, the proximal end of the needle hub 280 in the first needle position and the proximal end of the inner diameter of the handle 271 and the barrel 272. In this manner, silicone gel 291 can be easily and accurately applied by the user at the desired locations described in the embodiments above.

FIGS. 23-26 illustrate a fifth exemplary embodiment of a catheter assembly 310. The catheter assembly 310 of this embodiment is a blood control catheter assembly that uses many of the features described in the embodiments above. Specifically, the catheter assembly 310 includes a catheter 330, a catheter adapter 332 and a retention feature 334, as well as a needle 320, a needle deformation 322 and a sharp distal tip 324 in a similar manner as described above.

A mating portion 364 is disposed at a proximal end of the catheter adapter 332. The mating portion 364 permits fluid flow and receives or engages or abuts an end of a Luer connector or device (not shown). The mating portion 364 preferably allows fluid to be exchanged between the Luer connector and the catheter 330 during engagement.

The mating portion 364 advantageously includes a Luer engagement surface of at least 7.5 mm in length. Such a configuration satisfies recently updated ISO 594 standard, which is now ISO 80369-7, entitled Small-Bore Connector Standard. This new ISO standard controls size and variation of all small-bore connectors to reduce misconnection between the various standard sub-types, thus avoiding inaccurate Luer connections in the design of the catheter adapter 332. Accordingly, satisfying the new requirements of ISO 80369-7 invokes a greater need to optimize space and to develop a compact design of the catheter assembly 310.

Figure 31:
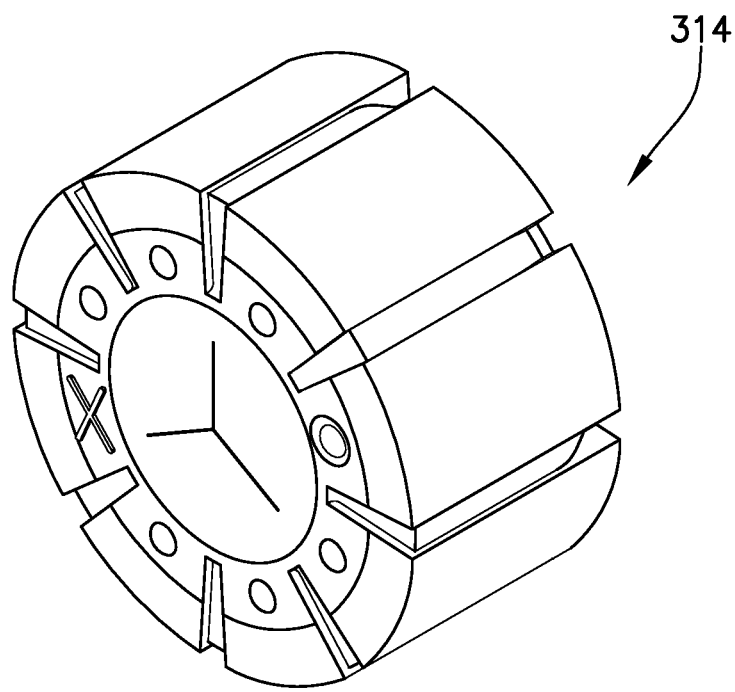
FIG. 31 illustrates a perspective view of a septum in the blood control catheter assembly of FIG. 23.

The catheter assembly 310 includes a septum 314 that regulates the flow of fluid. As best illustrated in FIG. 31, the septum 314 has one or more pre-formed openings or slits designed to selectively prevent unwanted fluid flow through the septum 314. Three intersecting slits forming three flaps open when engaged by a septum actuator 360, as described in detail below.

The septum 314 shown in FIG. 31 may be used in any of the embodiments discussed herein. Other septum configurations may be used as would be understood by one of ordinary skill in the art. The septum 314 is made of an elastic material to form the valve, for example silicone rubber. Other elastic materials may be used and non-elastic materials may be incorporated in the septum 314 as needed.

Figure 27:
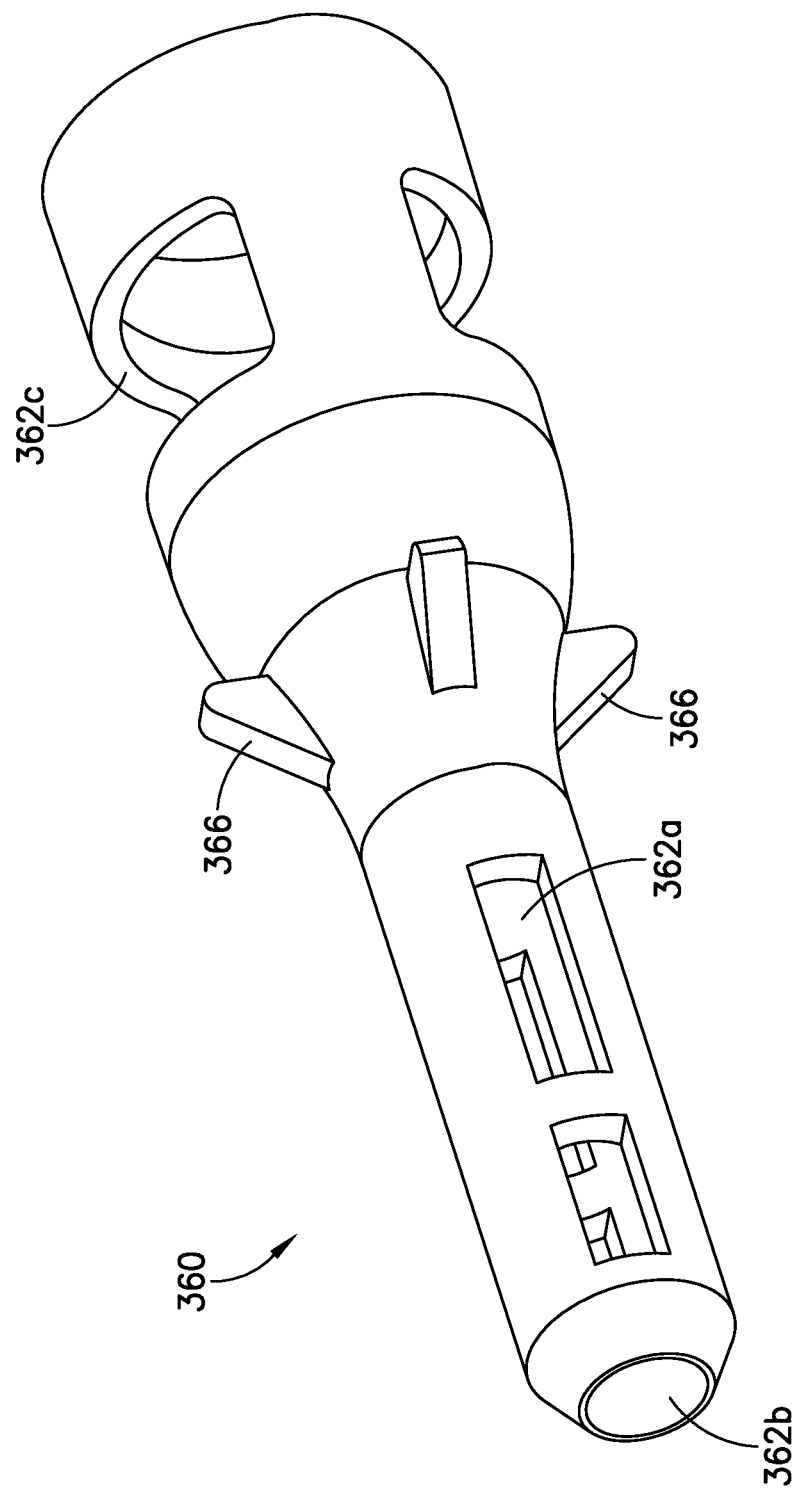
FIG. 27 illustrates a perspective view of a septum actuator of the blood control catheter assembly of FIG. 23.

The catheter assembly 310 further includes the septum actuator 360 as best illustrated in FIG. 27. Septum actuators 360 similar to that of FIG. 27 may be used in any of the embodiments described herein. The septum actuator 360 is positioned in the catheter adapter 332 and is axially moveable in the catheter adapter 332 to engage (open the slits of) and disengage (close the slits of) the septum 314. The septum actuator 360 is preferably made in one piece from a rigid or semi-rigid material, for example a rigid polymer material or a metal.

The septum actuator 360 includes an internal passage 362a that spans a full length of the septum actuator 360. The septum actuator 360 is a substantially tubular member and the internal passage 362a is substantially cylindrical to provide a hollow passage in the septum actuator 360 so that fluid can be exchanged through the septum 314 when the septum 314 is opened and/or penetrated by the septum actuator 360. The internal passage 362a is in fluid communication with the distal opening 362b disposed at the distal end of the septum actuator 360.

One or more openings 362c are disposed at various positions between the proximal and distal ends of the septum actuator 360. The openings 362c of the septum actuator 360 are similarly described in U.S. Pat. No. 9,101,746, which is hereby incorporated by reference in its entirety. These openings 362c act as flushing windows to provide fluid exchange and flushing in and through the septum actuator 360. Each of the openings 362c has a width larger than a width of the flexible arms 344 as further described below. The openings 362c extend through the septum actuator 360 in a direction substantially perpendicular to a centerline of the internal passage 362a. The openings 362c are in fluid communication with the internal passage 362a to permit fluid flow through and around the septum actuator 360.

The openings 362c advantageously provide increased area for the fluid to move inside the catheter adapter 332 of the catheter assembly 310. The increased area advantageously allows for fluid flushing and to prevent coagulation of fluid in the proximal and distal ends of the septum 314, as well as in the proximal and distal ends of the catheter adapter 332. As a result, the openings 362c advantageously minimize the stagnation of fluid and allow for greater mixing.

Finally, the openings 362c also advantageously and simultaneously allow engagement by a spring clip 340 as described below. Such an engagement between the spring clip 340 and the septum actuator 360 advantageously optimizes space and provides a compact design of the catheter assembly 310. A shorter length of the catheter assembly 310 normally creates reduced flushing performance. However, the embodiments of the catheter assembly 310 advantageously use the openings 362c of the septum actuator 360 in a dual manner of fluid flushing and interlocking with the spring clip 340 to achieve size benefits while maintaining optimal performance.

The septum actuator 360 also includes a flange 366 that engages the retention feature 334 in the catheter adapter 332. Specifically, an outer diameter of the flange 366 is larger than an inner diameter of the retention feature 334. Accordingly, the retention feature 334 restrains the septum actuator 360 in the catheter adapter 332 so that the septum actuator 360 and the spring clip 340 are not inadvertently displaced or removed.

After the catheter 330 is placed into the skin of the patient, the catheter assembly 310 can be accessed and/or used either once or multiple times by a practitioner. In the former case, the septum actuator 360 remains engaged with the septum 314 after the Luer connector is removed. In the latter case, the septum actuator 360 is configured to move between a first actuator position and a second actuator position. In the first actuator position, the septum actuator 360 pierces the septum 314 and establishes fluid communication with the catheter 330 and the proximal end of the catheter adapter 332. In the second actuator position, the septum actuator 360 no longer pierces the septum 314 prohibiting fluid communication between the catheter 330 and the proximal end of the catheter adapter 332.

The septum actuator 360 can move from the first actuator position to the second actuator position in a variety of ways. In one embodiment, a return member such as a spring (not shown) engages an inner diameter of the catheter adapter 332 and an outer diameter of the septum actuator 360. The spring is compressed when the septum actuator 360 moves into the first actuator position. After use, as further described below, spring force from the spring causes the septum actuator 360 to move from the first actuator position to the second actuator position.

In another embodiment, the elasticity of the septum 314 does not allow the septum actuator 360 to fully pierce the septum 314 in the first actuator position. Rather, the septum 314 is partially pierced by the septum actuator 360. Accordingly, after use, as further described below, the elasticity of the septum 314 provides a force that moves the septum actuator 360 to the second actuator position.

Figure 28:
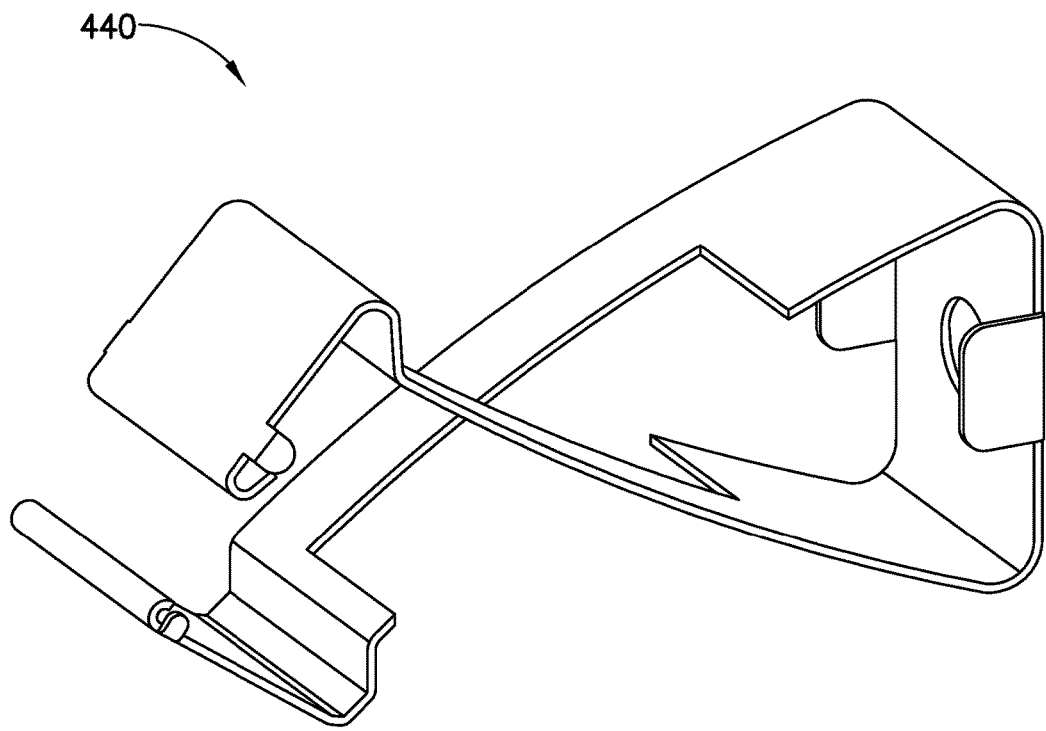
FIG. 28 illustrates a perspective view of a spring clip commonly used in a blood control catheter assembly of the prior art.
Figure 29:
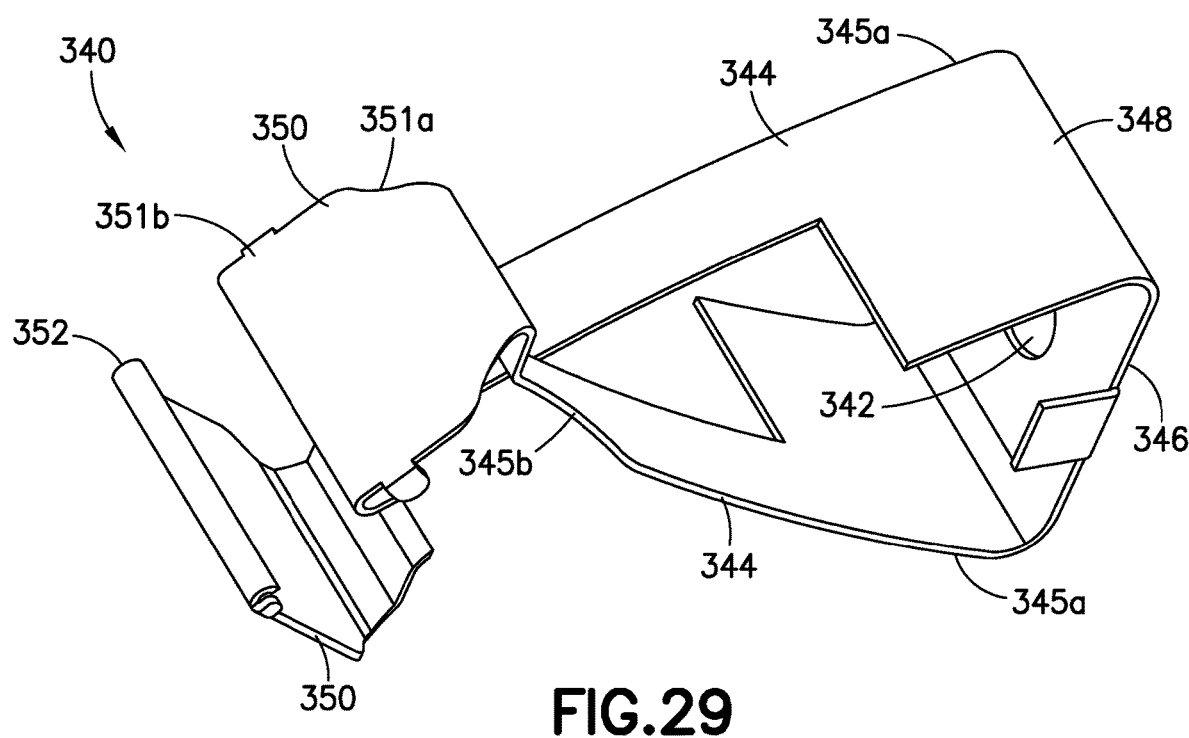
FIG. 29 illustrates a top perspective view of a spring clip in the blood control catheter assembly of FIG. 23.
Figure 30:
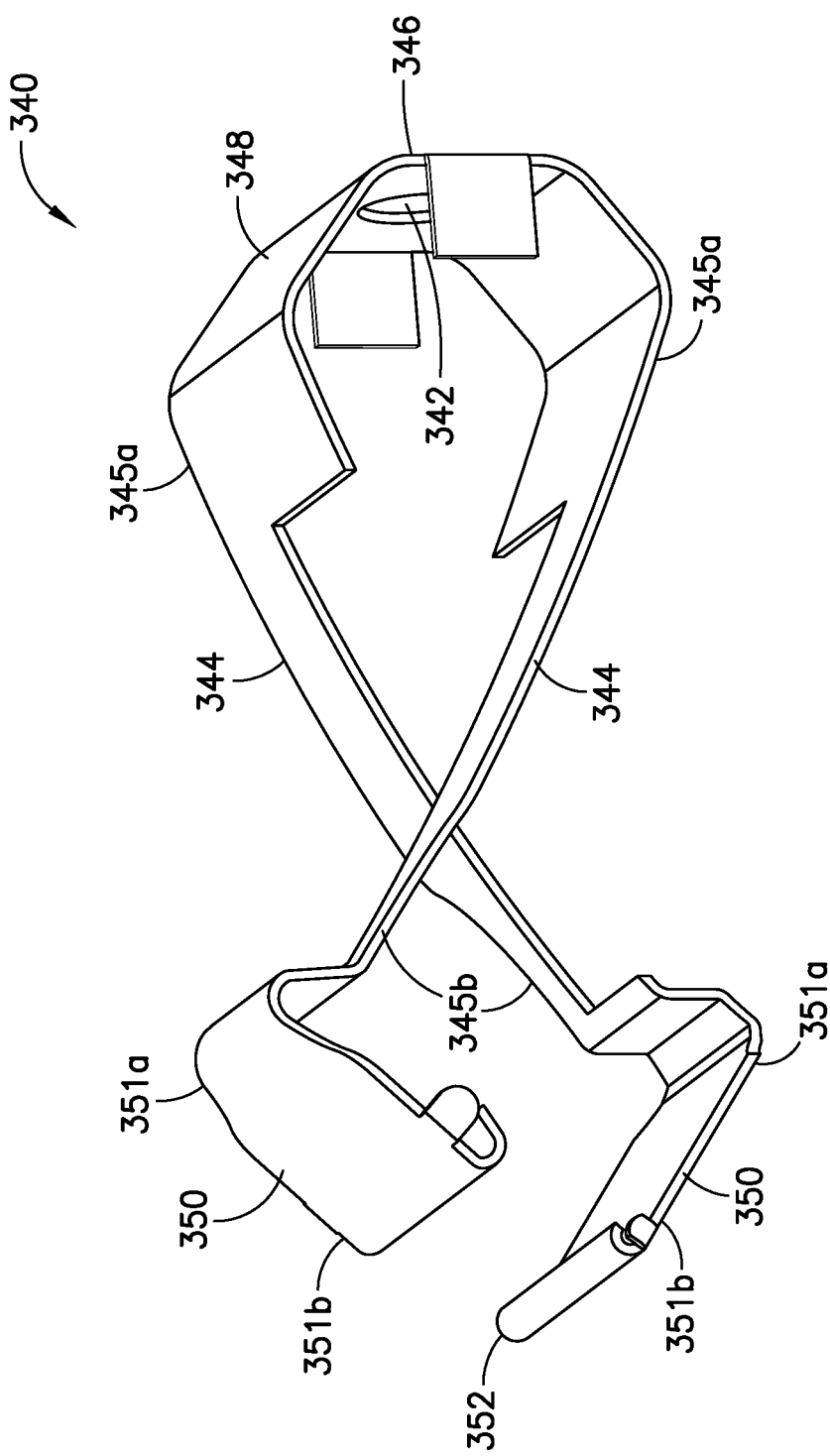
FIG. 30 illustrates a side perspective view of the spring clip in the blood control catheter assembly of FIG. 23.

The catheter assembly 310 further includes the spring clip 340 disposed in the septum actuator 360. The spring clip 340 includes many of the features described above such as an opening 342, flexible arms 344, a rear wall 346, a tapered outer surface 348, distal walls 350 and a lip 352. FIG. 28 illustrates a spring clip 440 known in the prior art, while FIGS. 29 and 30 illustrate the exemplary spring clip 340 in this embodiment of the catheter assembly 310. Further information about the spring clip 440 of the prior art as illustrated in FIG. 28 is disclosed in U.S. Pat. No. 8,337,463, which is hereby incorporated by reference in its entirety.

The flexible arms 344 in the spring clip 340 illustrated in FIGS. 29 and 30 include a proximal arm portion 345a and a distal arm portion 345b. The proximal arm portion 345a is wider than the distal arm portion 345b to advantageously provide the necessary flexibility and spring force during operation. The distal arm portion 345b includes a cutout having a curvature or section that is narrower than a remaining section of the distal arm portion 345b. This cutout in the distal arm portion 345b is not present in the spring clip 440 of the prior art as illustrated in FIG. 28.

FIGS. 29 and 30 also illustrate the distal walls 350 of the flexible arms 344 of the spring clip 340 to each include a top wall portion 351a and a bottom wall portion 351b. The top wall portion 351a is narrower than the bottom wall portion 351b. Specifically, the top wall portion 351a includes a cutout having a curvature or section, similarly to the distal arm portion 345b. Again, similar to the distal arm portion 345b, the cutout in the top wall portion 351a is not present in the spring clip 440 of the prior art as illustrated in FIG. 28.

The cutouts in the distal arm portion 345b and the top wall portion 351a meet at the highest section of the spring clip 340. The highest section of the spring clip 340 extends into and out of the openings 362c of the septum actuator 360 during operation. These cutouts are advantageously provided so that the flexible arms 344 can engage and disengage the openings 362c of the septum actuator 360 during operation while minimizing or eliminating contact with the openings 362c. Specifically, a width of the cutouts is advantageously smaller than a width of the openings 362c of the septum actuator 360 to allow proper operation.

Accordingly, no unnecessary friction is produced, the life of the spring clip 340 is optimized, and the spring clip 340 can operate without interference. Also, the spring clip 340 does directly contact or engage the catheter adapter 332 to advantageously optimize space and provide a compact design of the catheter assembly 310. Finally, the openings 362c of the septum actuator 360 are advantageously used in a dual manner of fluid flushing and interlocking with the spring clip 340 to achieve a compact design while maintaining optimal performance.

In another embodiment (not illustrated), the flexible arms of the spring clip are narrower than the flexible arms 344 of the spring clip 340 described above. The spring clip is narrow enough to engage and disengage the openings 362c of the septum actuator 360 in a similar manner as described above. Specifically, the narrower flexible arms replace the cutouts in the distal arm portion 345b and the top wall portion 351a of the spring clip 340 to achieve the same benefits and advantages as described above.

In a first needle position as similarly described in previous embodiments, the flexible arms 344 of the spring clip 340 are biased on the needle 320. In this embodiment, the flexible arms 344 protrude into or engage the openings 362c of the septum actuator 360. This engagement prevents removal of the spring clip 340 from the septum actuator 360.

In a second needle position as similarly described in previous embodiments, the flexible arms 344 of the spring clip 340 enclose the distal tip 324 of the needle 320. The spring clip 340 protects the distal tip 324 from further use or inadvertent contact. In this embodiment, the flexible arms 344 retract from and disengage the openings 362c of the septum actuator 360. This disengagement allows for the removal of the spring clip 340 from the septum actuator 360.

Accordingly, due to the disengagement described above, the spring clip 340 and the needle 320 can move from the second needle position to a third needle position. The third needle position separate and removes the spring clip 340 and the needle 320 from the catheter adapter 332 of the catheter assembly 310. Moving between the first, second and third needle positions can occur either manually or automatically as further described below.

Various alternative designs of the spring clip 340 are contemplated in this application, although not illustrated. For example, the spring clip 340 can be made of plastic, metal or a combination of both. A resilient band can be disposed around the spring clip 340 to assist in closing the spring clip 340 and enclosing the distal end of the needle 320. Examples of alternative spring clips are those described in U.S. Patent Application Publication Nos. 2012/0136311, 2013/0030391, 2013/0184645, 2013/0178800, 2014/0121604 and 2017/0043135, which are hereby incorporated by reference in their entirety. Any of these alternative spring clips can be modified to operate similarly to the spring clip 340 in the catheter assembly 310 disclosed herein.

Figure 24:
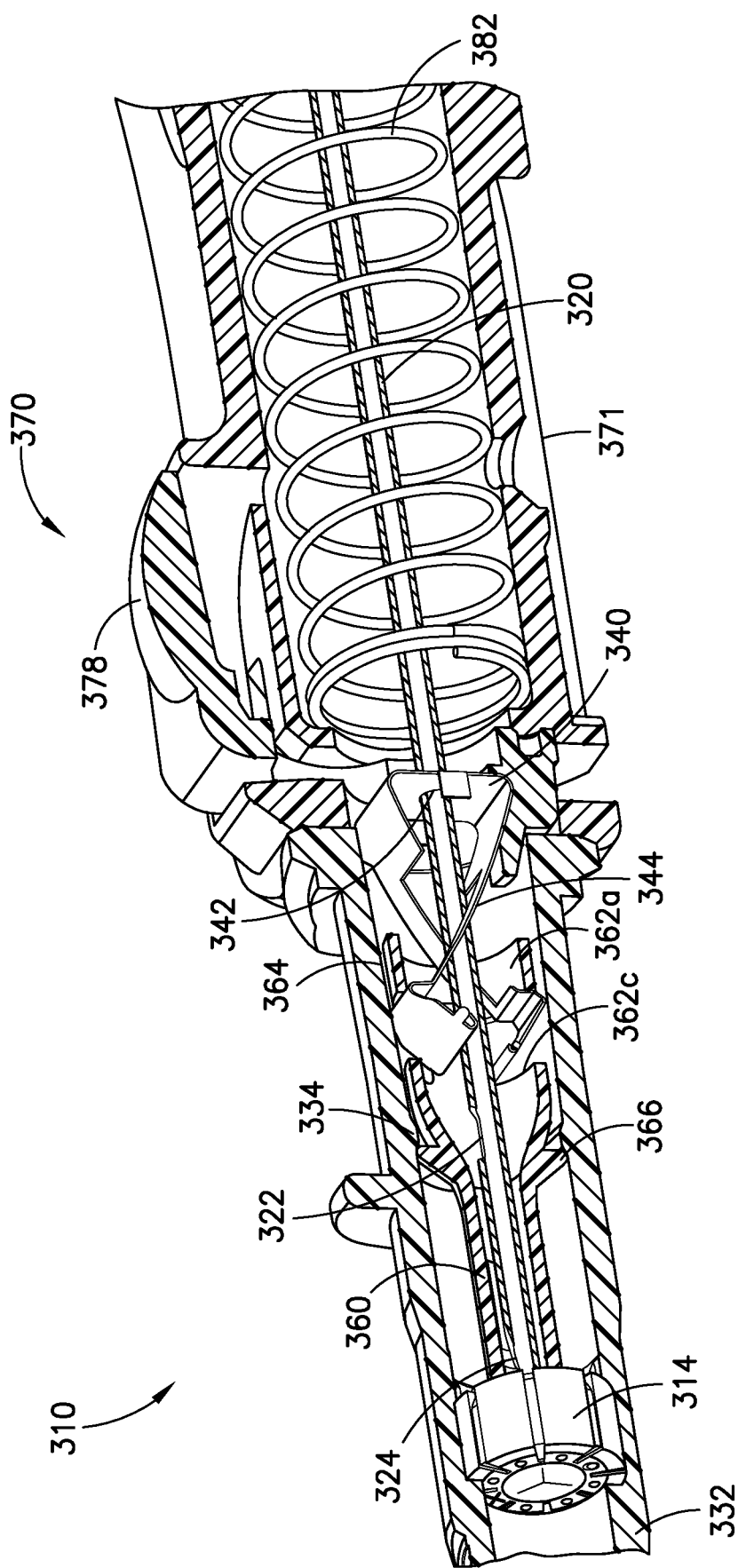
FIG. 24 illustrates a cross section view of the blood control catheter assembly of FIG. 23 with a barrel assembly.

FIG. 24 also illustrates a barrel assembly 370 optionally connected to the catheter assembly 310. The barrel assembly 370 includes a grip 371, an activation button 378 and a spring 382, as well as other features described above. The barrel assembly 370 provides automatic withdrawal of the needle 320 when moving from the first needle position to the second needle position and finally to the third needle position. In another embodiment of the catheter assembly 310, a barrel assembly is not present. Rather, the needle 320 is manually moved from the first needle position to the second needle position and ultimately to the third needle position by a user.

Figure 32:
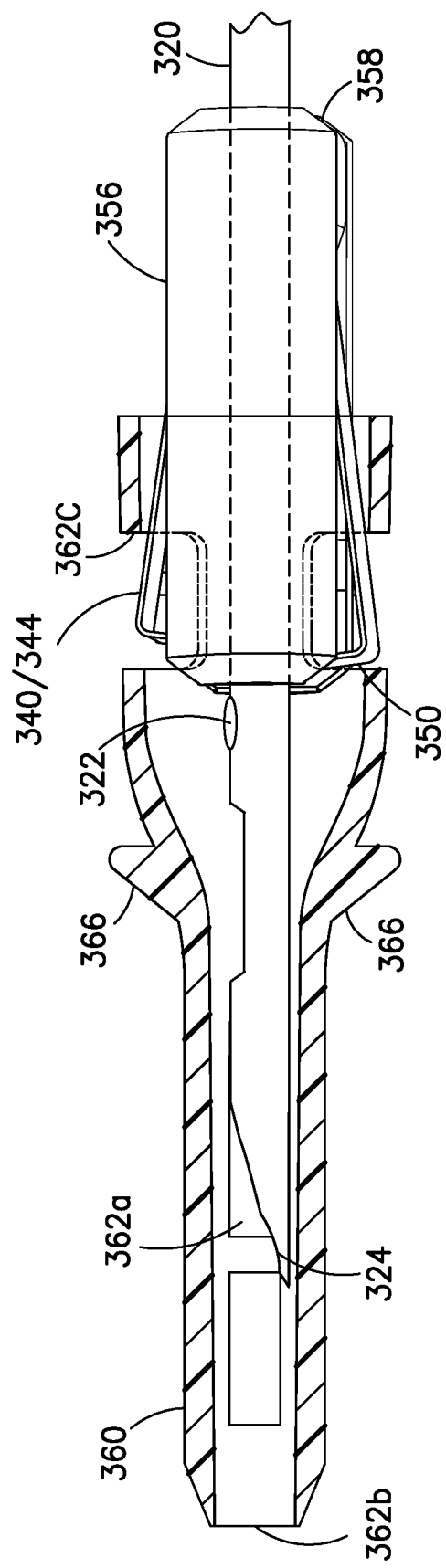
FIG. 32 illustrates a transparent perspective view of a spring clip and spring housing in a sixth exemplary embodiment of the blood control catheter assembly moving from a first needle position to a second needle position.

FIG. 32 illustrates a sixth exemplary embodiment of the catheter assembly 310 where the spring clip 340 is enclosed by a spring housing 356 in a similar manner as described above. The spring clip 340 and the spring housing 356 are disposed in the septum actuator 360 in the first and second needle positions of the catheter assembly 310. Subsequently, the spring clip 340, the spring housing 356 and the needle 320 are removed from the septum actuator 360 of the catheter assembly 310 in the third needle position.

The operation of the catheter assembly 310 is described below. The catheter 330 and the needle 320 are inserted into a vein of a patient in the first catheter assembly position. When the needle 320 and catheter 330 are securely disposed, the activation button 378 is depressed. Upon depression of the activation button 378, an inner needle hub and the spring 382 are disengaged from a wall (not illustrated in FIG. 24 but illustrated in previous embodiments) of the activation button 378. The needle 320 then retracts into the catheter adapter 332 via spring force from the spring 382. In another embodiment, when the needle 320 and catheter 330 are securely disposed, the needle 320 is withdrawn by a user manually and without the use of the barrel assembly 370.

Figure 23:
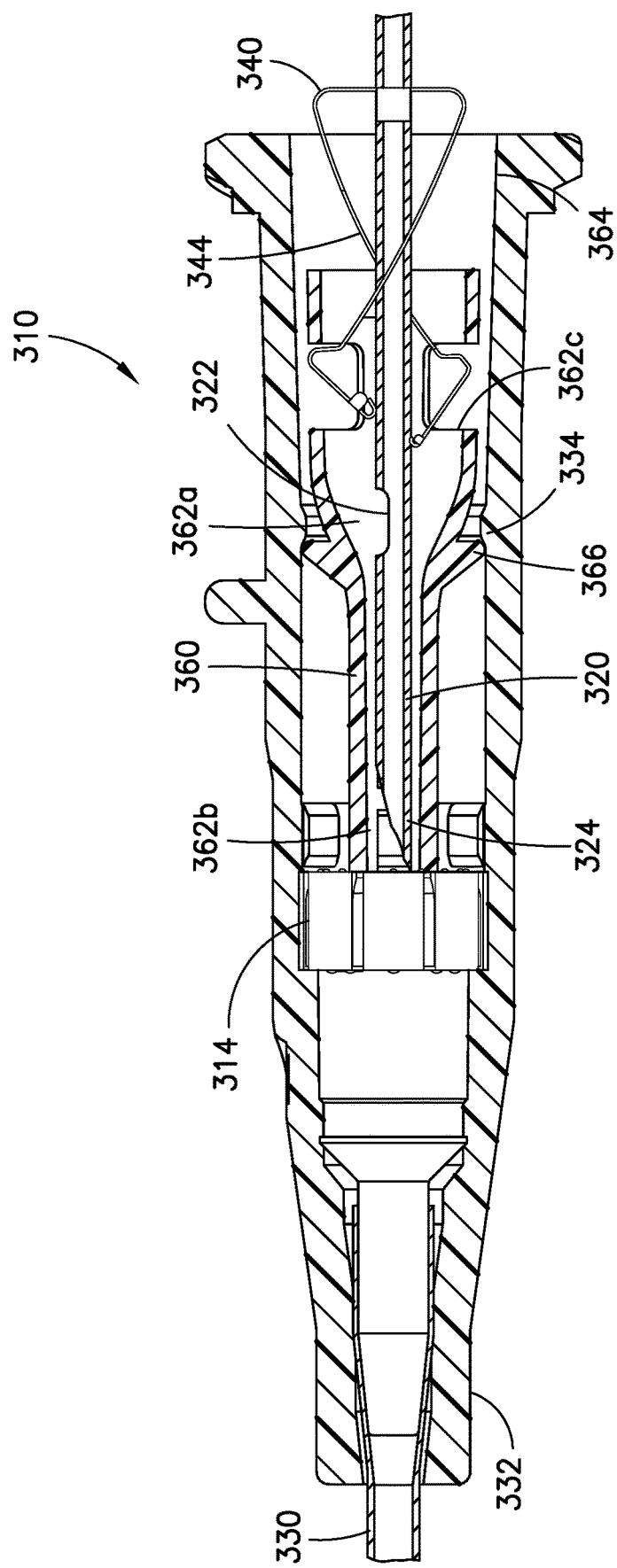
FIG. 23 illustrates a cross section view of a fifth exemplary embodiment of a blood control catheter assembly moving from a first needle position to a second needle position.

As the needle 320 retracts into the catheter adapter 332, either manually by the user or automatically via the barrel assembly 370, the distal tip 324 of the needle 320 no longer pierces the septum 314 as illustrated in FIG. 23. Accordingly, the septum 314 forms a fluid-tight seal and selectively prohibits fluid exchange to or from the catheter 330. In other words, the septum 314 selectively permits or blocks the flow of fluid through the catheter 330 based on whether the septum 314 is pierced by the septum actuator 360.

Figure 25:
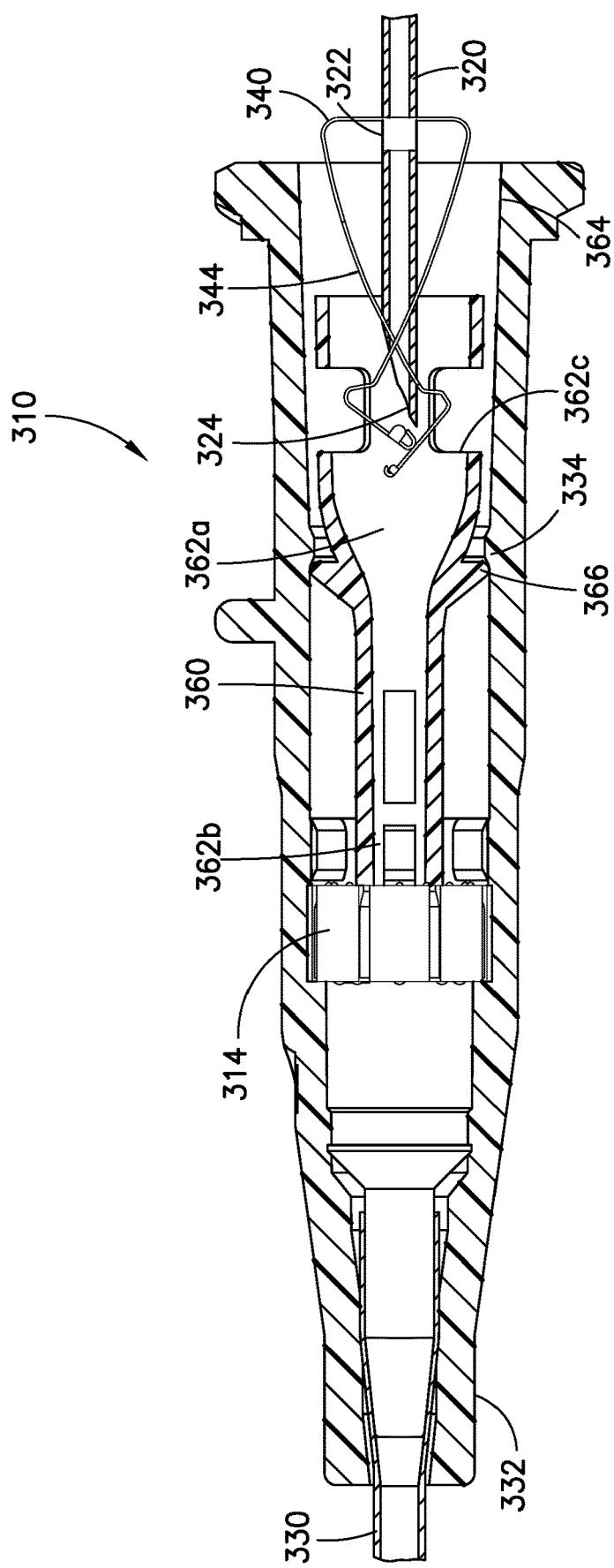
FIG. 25 illustrates a cross section view of the blood control catheter assembly of FIG. 23 in the second needle position.

The needle 320 subsequently enters into the second needle position as illustrated in FIG. 25 where the distal tip 324 of the needle 320 is enclosed by the spring clip 340. As described above, the flexible arms 344 of the spring clip 340 are biased by the needle 320 in the first needle position. When the needle 320 enters into the second needle position, the lips 352 of the spring clip 340 are no longer biased on the needle 320 and instead contact each other to enclose and shield the distal tip 324 of the needle 320. As described above, the needle 320 enters into the second needle position either manually by the user or automatically using the barrel assembly 370.

In the second needle position, the flexible arms 344 also disengage from the openings 362c of the septum actuator 360. Specifically, the highest portion of the spring clip 340 where the cutouts in the distal arm portion 345b and the top wall portion 351a meet no longer protrudes from the openings 362c of the septum actuator 360. This disengagement allows the needle 320 and the spring clip 340 to be removed from the catheter adapter 332 as described below.

Next, the needle 320 moves to the third needle position. When the catheter assembly 310 is cooperating with the barrel assembly 370 as illustrated in FIG. 24, the spring 382 surrounding the inner needle hub is released by the activation button 378 as described above. This causes the inner needle hub to travel to the proximal, opposite end of the barrel assembly 370 (not illustrated in FIG. 24 but illustrated in previous embodiments). Thus, the needle 320 is now in a retracted, third needle position, where the complete needle 320 (including its sharp distal tip) and the spring clip 340 are retained in the outer housing of the barrel assembly 370. The inner needle hub holding the needle 320 is retained in the outer housing of the barrel assembly 370 via the force exerted by the spring 382. Accordingly, the combination of the inner needle hub, the outer housing and the spring 382 is an exemplary needle protection member to enclose the needle 320.

Figure 26:
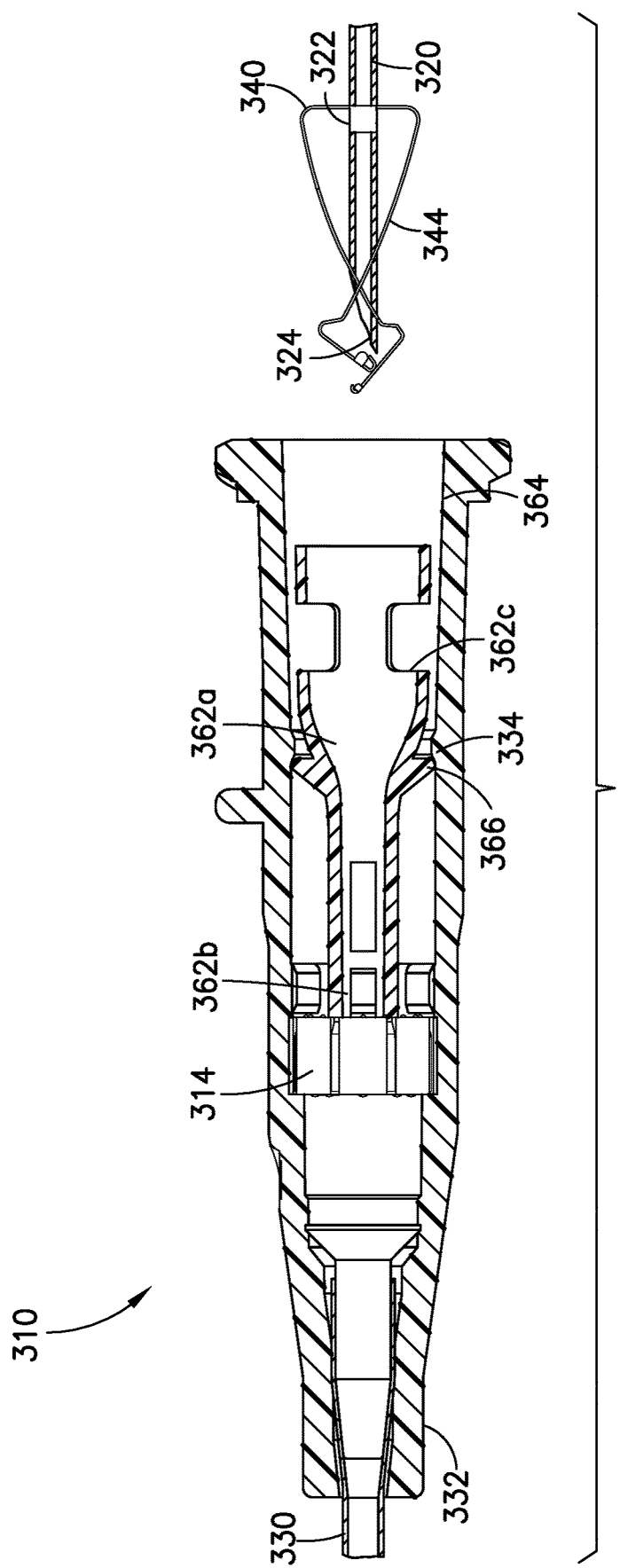
FIG. 26 illustrates a cross section view of the blood control catheter assembly of FIG. 23 in a third needle position.

Alternately, as illustrated in FIG. 26, the needle 320 can move to the third needle position manually by the user. Specifically, since the spring clip 340 is now disengaged from the septum actuator 360, the user can manually pull the needle 320 out of the catheter assembly 310. The needle deformation 322 in the needle 320 causes the spring clip 340 to be removed with the needle 320 in a similar manner described above.

After initial use of the needle 320, further use of the catheter assembly 310 is described as follows. When the catheter 330 is initially inserted into a patient, the needle 320 is removed and the septum 314 prevents blood from flowing out of the proximal end of the catheter adapter 332. As a male Luer connector is inserted in the catheter adapter 332, the end of the Luer connector abuts the septum actuator 360. Further movement of the Luer connector moves the septum actuator 360 into the first actuator position axially toward and engages the septum 314. As the septum 314 is pierced (partially or fully), the distal end of the septum actuator 360 separates one or more of the slits to engage and open the septum 314. After the septum 314 is opened by the septum actuator 360, fluid is permitted to flow from the Luer connector, through internal passages 362a, the distal opening 362b and the openings 362c of the septum actuator 360, and ultimately into the catheter 330 or vice versa.

When the Luer connector is removed, the septum actuator 360 disengages the septum 314 via the elastic force from the septum 314 (or spring force as described above) and returns to the second actuator position. The septum actuator 360 is restrained from moving beyond the second actuator position due to the engagement between the flange 366 of the septum actuator 360 and the retention feature 334 in the catheter adapter 332.

Alternately, the septum actuator 360 remains engaged to the septum 314 when the Luer connector is removed. Subsequently, the catheter assembly 310 is discarded after use.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A spring clip for a catheter assembly, the spring clip comprising:
   first and second flexible arms, each configured to open and close the spring clip by a needle biasing the spring clip in an open position and releasing the spring clip to enclose a distal tip of the needle in a closed position;
   an opening for the needle to pass through;
   a distal wall having a lip provided on each of the first and second flexible arms, the needle biasing the lip in the open position, and the distal wall and the lip blocking the distal tip of the needle in the closed position, each of the distal walls includes a top wall portion and a bottom wall portion, the top wall portion is narrower in width than the bottom wall portion; and
   a rear wall connecting the first and second flexible arms; wherein
   the first flexible arm includes a cutout section facing opposite to the second flexible arm.

2. The spring clip of claim 1, wherein
   the first and second flexible arms each include a proximal arm portion and a distal arm portion;
   the distal arm portion is narrower in width than the proximal arm portion; and
   the distal arm portion of the first flexible arm includes the cutout section.

3. The spring clip of claim 1, wherein the top wall portion includes the cutout section.

4. The spring clip of claim 1, wherein the cutout section is disposed between the top wall portion of the distal wall of the first flexible arm, and a distal arm portion of the first flexible arm.

5. The spring clip of claim 1, wherein the second flexible arm includes another cutout section facing opposite to the first flexible arm.

6. The spring clip of claim 1, wherein the rear wall includes a tapered outer surface that is configured to guide movement of the spring clip into a barrel assembly.

7. The spring clip of claim 1, wherein the cutout section has a curvature.

8. A catheter assembly comprising:
   a catheter connected to a catheter adapter;
   a needle having a distal tip and disposed in the catheter such that in a first needle position, the needle extends beyond the catheter;
   a septum actuator having an opening, the septum actuator disposed in the catheter adapter and configured to open a septum; and
   a spring clip disposed in the septum actuator and engaging the opening of the septum actuator in the first needle position, the spring clip includes first and second flexible arms, each configured to open and close the spring clip, a distal wall having a lip provided on each of the first and second flexible arms, the needle biasing the lip in the open position, and the distal wall and the lip blocking the distal tip of the needle in the closed position, each of the distal walls includes a top wall portion and a bottom wall portion, the top wall portion is narrower in width than the bottom wall portion.

9. The catheter assembly of claim 8, wherein
   the septum activator has more than one opening; and
   the first flexible arm includes a cutout section facing opposite to the second flexible arm.

10. The catheter assembly of claim 9, wherein the cutout section does not contact a sidewall of the opening of the septum actuator.

11. The catheter assembly of claim 9, wherein the first and second flexible arms disengage the openings of the septum actuator in a second needle position to allow removal of the spring clip from the catheter assembly.

12. The catheter assembly of claim 9, wherein
   the first and second flexible arms each include a proximal arm portion and a distal arm portion;
   the distal arm portion is narrower in width than the proximal arm portion; and
   the distal arm portion of the first flexible arm includes the cutout section.

13. The catheter assembly of claim 9, wherein the top wall portion includes the cutout section.

14. The catheter assembly of claim 9, wherein the cutout section is disposed between the top wall portion of the distal wall of the first flexible arm, and a distal arm portion of the first flexible arm.

15. The catheter assembly of claim 9, wherein the second flexible arm includes another cutout section facing opposite to the first flexible arm.

16. The catheter assembly of claim 9, wherein
   the spring clip includes a rear wall; and
   the rear wall is connected to each of the first and second flexible arms; and
   the rear wall includes a tapered outer surface that is configured to guide movement of the spring clip into a barrel assembly.

17. The catheter assembly of claim 9, wherein the cutout section has a curvature.

18. The catheter assembly of claim 8, wherein when the needle is in a second needle position, the spring clip disengages the opening of the septum actuator.

* * * * *